US012721569B2

(12) United States Patent
Zhu et al.

(10) Patent No.: US 12,721,569 B2
(45) Date of Patent: Sep. 1, 2026

(54) SLEEP QUALITY ASSESSMENT AND IN-BED STATE MONITORING

(71) Applicant: Anhui Huami Health Technology Co., Ltd., Hefei (CN)

(72) Inventors: Guokang Zhu, Hefei (CN); Yi Zhang, Hefei (CN); Dening Hao, Hefei (CN); Xiaowei Dai, Hefei (CN); Kongqiao Wang, Hefei (CN)

(73) Assignee: Anhui Huami Health Technology Co., Ltd., Hefei (CN)

( * ) Notice: Subject to any disclaimer, the term of this patent is extended or adjusted under 35 U.S.C. 154(b) by 326 days.

(21) Appl. No.: 18/419,199

(22) Filed: Jan. 22, 2024

(65) Prior Publication Data

US 2024/0156397 A1 May 16, 2024

Related U.S. Application Data

(63) Continuation of application No. PCT/CN2022/105838, filed on Jul. 14, 2022.

(30) Foreign Application Priority Data

Aug. 26, 2021 (CN) ........................ 202110987315.X
Sep. 15, 2021 (CN) ........................ 202111082791.3

(51) Int. Cl.
*A61B 5/00* (2006.01)
*A61B 5/11* (2006.01)

(52) U.S. Cl.
CPC .......... *A61B 5/4815* (2013.01); *A61B 5/1116* (2013.01); *A61B 5/1118* (2013.01);
(Continued)

(58) Field of Classification Search
CPC ... A61B 5/4815; A61B 5/1116; A61B 5/1118; A61B 5/7267; A61B 5/7278;
(Continued)

(56) References Cited

U.S. PATENT DOCUMENTS

2012/0232414 A1* 9/2012 Mollicone .............. A61B 5/024
600/508
2016/0015315 A1 1/2016 Auphan et al.
(Continued)

FOREIGN PATENT DOCUMENTS

CN 109222950 A 1/2019
CN 110558934 A 12/2019
(Continued)

OTHER PUBLICATIONS

International Search Report and English Translation for International Application No. PCT/CN2022/105838 dated Sep. 26, 2022.

*Primary Examiner* — Justin Xu
(74) *Attorney, Agent, or Firm* — Young Basile Hanlon & MacFarlane, P.C.

(57) ABSTRACT

Provided are sleep quality assessment methods, apparatuses, electronic devices, and storage medium, and relates to the field of artificial intelligence and deep learning technologies, and in particular to sleep quality assessment methods, apparatuses, electronic devices, and storage medium. The method includes: determining sleep data of a subject; obtaining sleep feature data based on a reference core sleep period of the subject and the sleep data; and evaluating sleep quality of the subject based on the sleep feature data. The method assesses the sleep quality of the subject based on the sleep feature data extracted based on the reference core sleep period of the subject and the sleep data of the subject, takes into account individual factors of the subject in extracting the sleep feature data, thus providing a more accurate assessment of the sleep quality of the subject.

20 Claims, 6 Drawing Sheets

(52) U.S. Cl.
CPC .......... *A61B 5/7267* (2013.01); *A61B 5/7278* (2013.01); *A61B 2560/0431* (2013.01); *A61B 2562/0219* (2013.01)

(58) Field of Classification Search
CPC .... A61B 2560/0431; A61B 2562/0219; A61B 5/4812; A61B 5/681; A61B 5/7264; A61B 5/00
See application file for complete search history.

(56) References Cited

U.S. PATENT DOCUMENTS

| | | | | |
|---|---|---|---|---|
| 2017/0156666 | A1* | 6/2017 | Surbur | A61B 5/681 |
| 2020/0251206 | A1* | 8/2020 | Zeller | G16H 40/20 |
| 2022/0061701 | A1* | 3/2022 | Krishnan | A61B 5/7232 |
| 2022/0148708 | A1* | 5/2022 | Narayanan | G06N 3/0499 |
| 2023/0040102 | A1* | 2/2023 | Bonistalli | A61B 5/0022 |

FOREIGN PATENT DOCUMENTS

| | | | |
|---|---|---|---|
| CN | 112754443 | A | 5/2021 |
| CN | 112914506 | A | 6/2021 |

* cited by examiner

SLEEP QUALITY ASSESSMENT AND IN-BED STATE MONITORING

CROSS-REFERENCE TO RELATED APPLICATION(S)

The present application is a continuation of International Application No. PCT/CN2022/105838, filed on Jul. 14, 2022, which claims priority and benefit of Chinese Patent Application No. 202110987315.X, filed Aug. 26, 2021, and of Chinese Patent Application No. 202111082791.3, filed Sep. 15, 2021, the entire contents of both of which are incorporated herein by reference.

TECHNICAL FIELD

The present disclosure relates to the field of artificial intelligence and deep learning technologies, and in particular, to a method for sleep quality assessment, a method for in-bed state monitoring, and related apparatuses thereof.

BACKGROUND

Sleep, as a complex life behavior, is closely related to human health and occupies approximately one-third of a person's lifespan. However, the pace of modern life is generally accelerated, and the pressures of daily life and work is increasing, leading to an increasing prevalence of sleep deprivation, which significantly affects quality of people's daily life and even their physical health. Therefore, monitoring sleep quality and assessing sleep condition of human beings are of great significance in guiding timely treatment for poor sleep.

In the related technologies for sleep quality detection, polysomnography (PSG) is commonly used to assess the sleep quality of users. However, PSG-based sleep quality assessment mainly relies on prior knowledge from the medical field, emphasizing universality and generality, and lacks consideration for the personalized characteristics of user subgroups and individuals. As a result, it cannot accurately evaluate the sleep quality of user subgroups and individuals. For example, one of the sleep metrics used for sleep quality assessment is "falling asleep before 12 AM," which is not applicable to users in a single time zone and cannot cope with situations where individuals have daily routines that are opposite to the general population due to work-related factors and the like.

SUMMARY

The present disclosure provides a method for sleep quality assessment, a method for in-bed state monitoring, and related apparatuses thereof.

According to a first aspect of the present disclosure, a sleep quality assessment method is provided, including: determining sleep data of a subject; extracting sleep feature data based on a reference core sleep period of the subject and the sleep data; and evaluating sleep quality of the subject based on the sleep feature data.

In the technical solution, by determining the sleep data of the subject, extracting the sleep feature data based on the reference core sleep period of the subject and the sleep data, and performing sleep quality assessment based on the sleep feature data, the method assesses sleep quality of the subject based on the sleep feature data extracted based on the reference core sleep period of the subject and the sleep data of the subject, and takes individual factors of the subject into account in the extraction of the sleep feature data, thereby providing a more accurate assessment of the sleep quality of the subject.

According to a second aspect of the present disclosure, a method for in-bed state monitoring based on a wearable device is provided, including: acquiring an acceleration signal output by the wearable device for the predetermined time period; determining a motion feature of the subject during the predetermined time period based on the acceleration signal; determining a posture feature of the subject during the predetermined time period based on the acceleration signal; and determining an in-bed state of the subject during the predetermined time period based on the posture feature and the motion feature.

According to another aspect of the present disclosure, an apparatus for sleep quality assessment is provided, including: a determination module, configured to determine sleep data of a subject; an extraction module, configured to extract sleep feature data based on a reference core sleep period of the subject and the sleep data; and an evaluation module, configured to evaluate sleep quality of the subject based on the sleep feature data.

According to another aspect of the present disclosure, an electronic device is provided, including: at least one processor; and a memory communicatively coupled to the at least one processor; where the memory stores instructions executable by the at least one processor, and execution of the instructions by the at least one processor causes the at least one processor to perform the method of the first aspect.

According to another aspect of the present disclosure, a wearable device is provided, including: an acceleration sensor; one or more wearable accessories; at least one processor; and a memory communicatively coupled to the at least one processor; where the memory stores instructions executable by the at least one processor, and execution of the instructions by the at least one processor causes the at least one processor to perform the method of the second aspect.

According to another aspect of the present disclosure, a non-transitory computer readable storage medium is provided, having computer instructions stored thereon, where the computer instructions are configured to cause a computer to perform the method of the first aspect, or to perform the method of the second aspect.

According to another aspect of the present disclosure, a computer program product including a computer program is provided, the computer program, when executed by a processor, implements the method of the first aspect, or implements the method of the second aspect.

It should be understood that the content described in this section is not intended to identify key or important features of the implementations disclosed herein, nor is it intended to limit the scope of the present disclosure. Other features of the present disclosure will become readily apparent through the following description.

BRIEF DESCRIPTION OF THE DRAWINGS

Drawings are provided to better understand the present disclosure and are not intended to limit the present disclosure.

DETAILED DESCRIPTION

Figure 1:
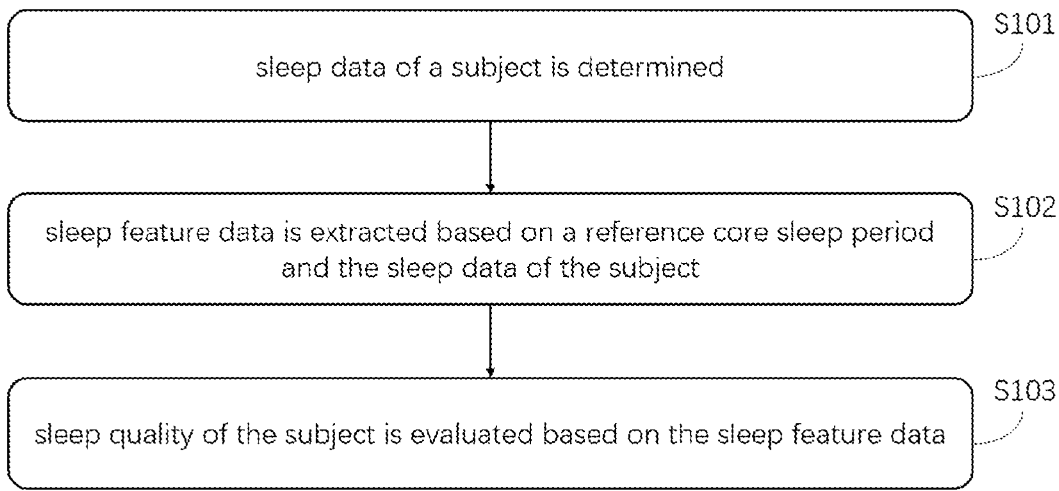
FIG. 1 is a schematic diagram of a method for sleep quality assessment according to some implementations of the present disclosure.

Implementations of the present disclosure are described in detail below, and examples of the implementations are shown in the accompanying drawings, where identical or similar reference numerals throughout represent identical or similar elements or represent elements with identical or similar functions. The implementations described below with reference to the drawings are illustrative and are intended for explanatory purposes in understanding the present disclosure, and should not be understood as limiting the present disclosure.

In the related technologies for sleep quality detection, polysomnography (PSG) is commonly used to assess the sleep quality of users. However, PSG-based sleep quality assessment mainly relies on prior knowledge from the medical field, emphasizing universality and generality, and lacks consideration for the personalized characteristics of user subgroups and individuals. As a result, it cannot accurately evaluate the sleep quality of user subgroups and individuals. For example, one of the sleep metrics used for sleep quality assessment is "falling asleep before 12 AM," which is not applicable to users in a single time zone and cannot cope with situations where individuals have daily routines that are opposite to the general population due to work-related factors and the like. On the other hand, the method for capturing physiological data using wearable devices for sleep quality analysis requires direct contact with the human body, which causes inconvenience and psychological burden to the subjects, leading to interference in their sleep process, affecting their sleep habits, and ultimately impacting the accuracy of sleep quality assessment for the subjects. Additionally, the evaluation models used in the method of capturing physiological data using wearable devices for sleep quality analysis mainly rely on manually established scoring rules for synthesizing various sleep features based on the domain knowledge of professionals, such as segmented linear weighting. These scoring rules provide a relatively coarse treatment of different sleep metrics and cannot accurately assess the sleep quality of users.

To address at least one of the above-mentioned issues, the present disclosure provides a method for sleep quality assessment, a method for in-bed state monitoring, and related apparatuses thereof.

FIG. 1 is a schematic diagram of a method for sleep quality assessment according to some implementations of the present disclosure. It should be noted that, the method for sleep quality assessment provided in the implementations of the present disclosure can be applied to the apparatus for sleep quality assessment provided in the implementations of the present disclosure, and the apparatus can be configured within electronic devices. The electronic devices can be a mobile terminal, such as a smartphone, a tablet, a personal digital assistant or other hardware devices with various operating systems. For example, the electronic devices can include an electronic device 1100 to be described below in conjunction with FIG. 11.

As shown in FIG. 1, the method for sleep quality assessment includes the following procedures.

At S101, sleep data of a subject is determined.

In some implementations of the present disclosure, the sleep data of the subject can be determined based on physiological data of the subject. For example, the apparatus for sleep quality assessment can acquire physiological data of the subject and determine the sleep data of the subject based on the physiological data. The physiological data may include one or more of pulse rate, respiratory rate, heart rate, etc., and the sleep data may include one or more of sleep duration, deep sleep duration, a number of sleep interruptions, etc.

At S102, sleep feature data is extracted based on a reference core sleep period and the sleep data of the subject.

In some implementations of the present disclosure, the reference core sleep period includes at least one of an individual core sleep period of the subject, or a collective core sleep period of a group in the designated area of the subject. The individual core sleep period of the subject may indicate the sleep habit or circadian rhythm of the subject, and may include a statistic result of the sleep time period for the subject during a certain period of time, where the statistic result of the sleep time period for the subject may be a time interval between an average time point for the subject to go to sleep (i.e., an average bedtime) and an average time point for the subject to wake up (i.e., an average wake-up time), or an average daily sleep time period over a certain period of time, or the like. Similarly, the collective core sleep period may indicate the sleep habit or circadian rhythm of a group of population in the area to which the subject belongs, and may include a statistic result of the sleep time period for at least a part of the population in the area to which the subject belongs during a certain period of time. For example, the individual core sleep period of the subject is from 10 PM to 6 AM within the last 180 days, and the collective core sleep period of a group within the designated area of the subject is also from 10 PM to 6 AM within the last 180 days. In some implementations, the reference core sleep period can be updated periodically or responsive to occurrence of a specific event. For example, the reference core sleep period is obtained from the sleep data of the subject for a recent time period of a certain duration, such as 90 days or the like.

In some implementations, during the extraction of sleep feature data based on the reference core sleep period and the sleep data of the subject, the extracted sleep feature data may vary depending on the reference core sleep period of the subject.

As an example, the reference core sleep period includes the individual core sleep period of the subject. A first sleep feature of the subject can be determined based on the individual core sleep period and the sleep data of the subject during the preset time period, and the first sleep feature is considered as at least part of the extracted sleep feature data. The first sleep feature may include at least one of the following features: sleep duration of the subject within the individual core sleep period, a proportion of the sleep duration to a total sleep duration of the subject, a deep sleep duration of the subject within the individual core sleep period, a number of deep sleep episodes of the subject within the individual core sleep period, a ratio of deep sleep duration to light sleep duration of the subject within the individual core sleep period, an awake duration of the subject within the individual core sleep period, a number of awake episodes of the subject within the individual core sleep period, or a proportion of the awake duration to the sleep duration of the subject within the individual core sleep period.

As another example, the reference core sleep period includes a collective core sleep period of a group in the designated area of the subject. A second sleep feature of the subject can be determined based on the collective core sleep period of the group within the designated area of the subject and the sleep data of the subject, and the second sleep feature is considered as at least part of the extracted sleep feature data. The second sleep feature may include at least one of the following features: a sleep duration the subject within the collective core sleep period, a proportion of the sleep duration to a total sleep duration of the subject, a deep sleep duration of the subject within the collective core sleep period, a number of deep sleep episodes of the subject within the collective core sleep period, a ratio of deep sleep duration to light sleep duration of the subject within the collective core sleep period, an awake duration of the subject within the collective core sleep period, a number of awake episodes of the subject within the collective core sleep period, or a proportion of the awake duration to the sleep duration of the subject within the collective core sleep period.

As another example, the reference core sleep period includes both the individual core sleep period of the subject and the collective core sleep period of a group in the designated area of the subject. The first sleep feature of the subject can be determined based on the individual core sleep period during the preset time period and the sleep data of the subject, and the second sleep feature of the subject can be determined based on collective core sleep period of the group within the designated area of the subject and the sleep data of the subject. Both the determined first and second sleep features are used to determine the sleep feature data of the subject.

At S103, sleep quality of the subject is evaluated based on the sleep feature data.

Optionally, the sleep quality of the subject is assessed based on the sleep feature data and a sleep quality assessment model. For instance, the sleep feature data is input into the sleep quality assessment model, and a sleep quality score is output. In some implementations, the sleep feature data is pre-processed before being input into the sleep quality assessment model. In some implementations, one or more sleep parameters indicating sleep quality are output, such as sleep efficiency or the like. For another instance, the sleep feature data and at least one other parameter are input into the sleep quality assessment model, the at least one other parameter may include user attribute information, the reference core sleep period, or the like.

Therefore, by determining the sleep data of the subject, extracting one or more sleep feature data based on a reference core sleep period and the sleep data of the subject, and evaluating the sleep quality of the subject based on the sleep feature data, the method evaluates the sleep quality of the subject based on the sleep feature data extracted according to the reference core sleep period and the sleep data of the subject, and the method takes into account individual factors of the subject during extraction of the sleep feature data, thereby providing a more accurate evaluation of the sleep quality of the subject.

Figure 2:
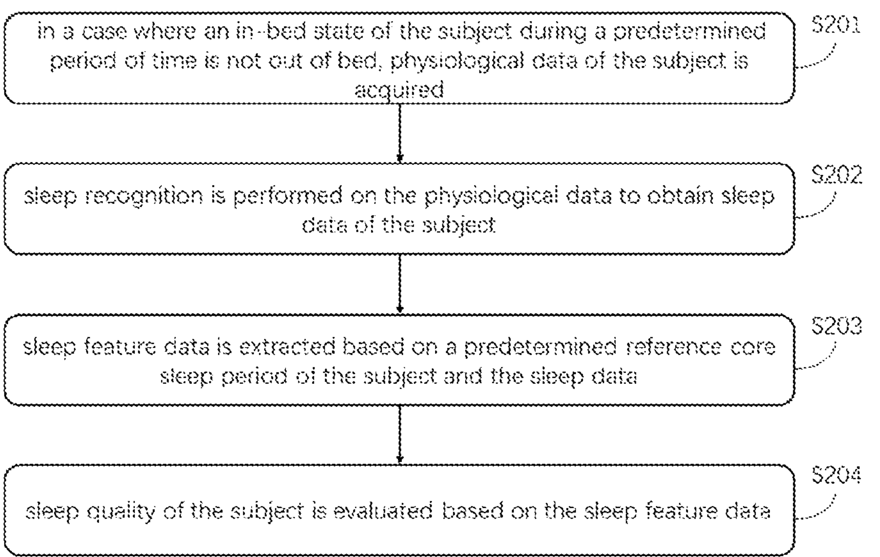
FIG. 2 is a schematic diagram of the method for sleep quality assessment according to some other implementations of the present disclosure.

In order to more accurately obtain the sleep data of the subject, as shown in FIG. 2, the method for sleep quality assessment according to some other implementations of the present disclosure is illustrated. In the implementations of the present disclosure, the sleep data of the subject may be acquired based on the physiological data of the subject, and the implementations shown in FIG. 2 includes the following procedures.

At S201, in a case where an in-bed state of the subject during a predetermined period of time is not out of bed, physiological data of the subject is acquired.

Before obtaining the sleep data of the subject, an in-bed state of the subject during a preset period of time can be determined, and the manner of determining the in-bed state of the subject during the predetermined time period can be found in the description of the subsequent implementations.

In some implementations of the present disclosure, if the in-bed state of the subject during the predetermined period of time is not out of bed, the apparatus for sleep quality assessment monitors and acquires physiological data of the subject, such as pulse rate, respiratory rate, heart rate and/or the like.

At S202, sleep recognition is performed on the physiological data to obtain sleep data of the subject.

Further, sleep recognition can be performed on the physiological data to obtain sleep data of the subject. For example, when a human body is in a sleep state, the respiratory rate decreases, so if a decrease in the respiratory rate is detected, it is determined that the subject is in a sleep state, and a duration of the sleep state is taken as the sleep duration of the subject. In another example, the heart rate can be used for sleep recognition to determine a duration of deep sleep and a number of sleep interruptions of the subject.

At S203, sleep feature data is extracted based on a predetermined reference core sleep period of the subject and the sleep data.

At S204, sleep quality of the subject is evaluated based on the sleep feature data.

S203 and S204 can each be implemented in any manner as described in various implementations of the present disclosure, and the implementations of the present disclosure are not limited thereto and will not be repeated herein.

Therefore, the sleep data of the subject can be accurately obtained by obtaining the physiological data of the subject and performing sleep recognition on the physiological data, thereby allowing accurate acquisition of the sleep data of the subject.

Figure 3:
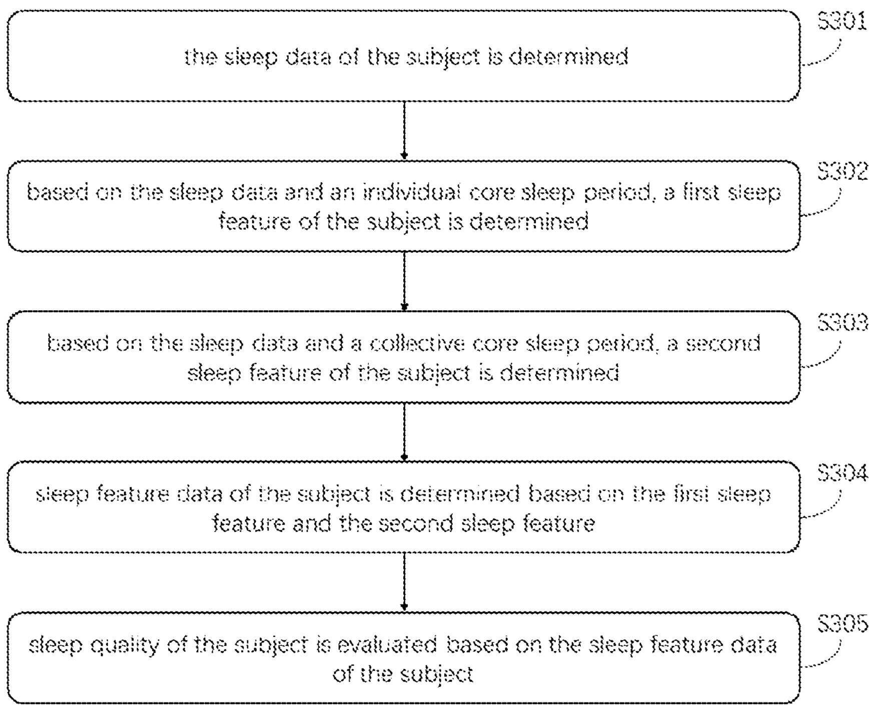
FIG. 3 is a schematic diagram of the method for sleep quality assessment according to some other implementations of the present disclosure.

In order to accurately determine the sleep feature data of the subject, as shown in FIG. 3, the method for sleep quality assessment according to some other implementations of the present disclosure is illustrated. In some implementations of the present disclosure, the reference core sleep period includes both the individual core sleep period of the subject and the collective core sleep period of the group within the designated area of the subject. The first sleep feature of the subject can be determined based on the individual core sleep period and the sleep data of the subject, and the second sleep feature of the subject can be determined based on collective core sleep period of the group within the designated area of the subject and the sleep data of the subject. Both the determined sleep features are used to determine the sleep feature data of the subject. The implementation shown in FIG. 3 may include the following procedures.

At S301, the sleep data of the subject is determined.

At S302, based on the sleep data and an individual core sleep period, a first sleep feature of the subject is determined.

In some implementations of the present disclosure, the first sleep feature may include at least one of the following features: sleep duration of the subject within the individual core sleep period, a proportion of the sleep duration of the subject within the individual core sleep period to a total sleep duration of the subject, a deep sleep duration of the subject within the individual core sleep period, a number of deep sleep episodes of the subject within the individual core sleep period, a ratio of deep sleep duration of the subject within the individual core sleep period to light sleep duration of the subject within the individual core sleep period, an awake duration of the subject within the individual core sleep period, a number of awake episodes of the subject within the individual core sleep period, or a proportion of the awake duration of the subject within the individual core sleep period to the sleep duration of the subject within the individual core sleep period.

The sleep duration of the subject within the individual core sleep period may be an overlapping duration between the sleep period of the subject in the sleep data and the individual core sleep period. For example, if the sleep data indicates that the subject goes to sleep at 11 PM and wakes up at 8 AM on the next day, the sleep period of the subject is from 11 PM to 8 AM, and if the individual core sleep period is from 10 PM to 6 AM, the overlapping duration between the sleep period of the subject and the individual core sleep period is a total of 7 hours from 11 PM to 6 AM, i.e., the sleep duration of the subject within the collective core sleep period is 7 hours. The proportion of the sleep duration of the subject within the collective core sleep period to the total sleep duration of the subject may be a ratio of the sleep duration of the subject within the individual core sleep period to the total sleep duration of the subject. For example, the sleep duration of the subject within the individual core sleep period is from 11 PM to 6 AM, and the total sleep duration of the subject is from 11 PM to 7 AM, then the ratio of the sleep duration of the subject within the collective core sleep period to the total sleep duration of the subject is 7/8. The deep sleep duration of the subject within the individual core sleep period is a total duration during which the subject is in deep sleep within the individual core sleep period. The number of deep sleep episodes of the subject within the individual core sleep period may be a total number of times the subject enters into deep sleep state within the individual core sleep period. The ratio of the deep sleep duration to light sleep duration of the subject within the individual core sleep period may be a ratio of a total duration during which the subject is in deep sleep to a total duration during which the subject is in light sleep within the individual core sleep period. The awake duration of the subject within the individual core sleep period is a total duration during which the subject enters an awake state within the individual core sleep period. The number of awake episodes of the subject within the individual core sleep period is a total number of times the sleep of the subject is interrupted and the subject enters the awake state within the individual core sleep period. The ratio of the awake duration to the total sleep duration of the subject within the individual core sleep period is a ratio of a total duration during which the sleep of the subject is interrupted and the subject enters an awake state to a total duration during which the subject is in a sleep state within the individual core sleep period.

At S303, based on the sleep data and a collective core sleep period, a second sleep feature of the subject is determined.

The second sleep feature may include at least one of the following characteristics: a sleep duration of the subject within the collective core sleep period, a proportion of the sleep duration of the subject within the collective core sleep period to a total sleep duration of the subject, a deep sleep duration of the subject within the collective core sleep period, a number of deep sleep episodes of the subject within the collective core sleep period, a ratio of deep sleep duration within the collective core sleep period to light sleep duration of the subject within the collective core sleep period, an awake duration of the subject within the collective core sleep period, a number of awake episodes of the subject within the collective core sleep period, or a proportion of the awake duration within the collective core sleep period to the sleep duration of the subject within the collective core sleep period.

The sleep duration of the subject within the collective core sleep period may be an overlapping duration between the sleep period of the subject in the sleep data and the collective core sleep period. For example, if the sleep data indicates that the subject goes to sleep at 11 PM and wakes up at 8 AM on the next day, the sleep period of the subject is from 11 PM to 8 AM, and if the collective core sleep period is from 10 PM to 6 AM, the overlapping duration between the sleep period of the subject and the collective core sleep period is a total of 7 hours from 11 PM to 6 AM, i.e., the sleep duration of the subject within the collective core sleep period is 7 hours. The proportion of the sleep duration of the subject within the collective core sleep period to the total sleep duration of the subject may be a ratio of the sleep duration of the subject within the collective core sleep period to the total sleep duration of the subject. For example, if the sleep duration of the subject within the collective core sleep period is from 11 PM to 6 AM, and the total sleep duration of the subject is from 11 PM to 7 AM, then the ratio of the sleep duration of the subject within the collective core sleep period to the total sleep duration of the subject is 7/8, i.e., the proportion of the sleep duration of the subject within the collective core sleep period to the total sleep duration of the subject is 7/8. The deep sleep duration of the subject within the collective core sleep period is a total duration of time during which the subject is in deep sleep within the collective core sleep period. The number of deep sleep episodes of the subject within the collective core sleep period may be a total number of times the subject enters into the deep sleep state within the collective core sleep period. The ratio of the deep sleep duration to light sleep duration of the subject within the collective core sleep period may be a ratio of a total duration of time during which the subject is in deep sleep within the collective core sleep period to a total duration of time during which the subject is in light sleep within the collective core sleep period. The awake duration of the subject within the collective core sleep period is a total duration of time during which the subject enters an awake state within the collective core sleep period. The number of awake episodes of the subject within the collective core sleep period is a total number of times the sleep of the subject is interrupted and the subject enters the awake state within the collective core sleep period. The ratio of the awake duration within the collective core sleep period to the total sleep duration of the subject within the collective core sleep period is a ratio of a total duration of time during which the sleep of the subject is interrupted and the subject enters an awake state within the collective core sleep period to a total duration of time during which the subject is in a sleep state within the collective core sleep period.

At S304, sleep feature data of the subject is determined based on the first sleep feature and the second sleep feature.

Optionally, the first sleep feature and the second sleep feature are concatenated to determine the sleep feature data of the subject. For example, the sleep feature data of the subject includes at least one of: a sleep duration the subject within the collective core sleep period, a proportion of the sleep duration to a total sleep duration of the subject, a deep sleep duration of the subject within the collective core sleep period, a number of deep sleep episodes of the subject within the collective core sleep period, a ratio of deep sleep duration to light sleep duration of the subject within the collective core sleep period, an awake duration of the subject within the collective core sleep period, a number of awake episodes of the subject within the collective core sleep period, a proportion of the awake duration to the sleep duration of the subject within the collective core sleep period, a sleep duration the subject within the collective core sleep period, a proportion of the sleep duration to a total sleep duration of the subject, a deep sleep duration of the subject within the collective core sleep period, a number of deep sleep episodes of the subject within the collective core sleep period, a ratio of deep sleep duration to light sleep duration of the subject within the collective core sleep period, an awake duration of the subject within the collective core sleep period, a number of awake episodes of the subject within the collective core sleep period, or a proportion of the awake duration to the sleep duration of the subject within the collective core sleep period.

At S305, sleep quality of the subject is evaluated based on the sleep feature data of the subject.

S301 and S305 can be implemented in any way as described in various implementations of the present disclosure, and the implementations of the present disclosure are not limited thereto and will not be repeated herein.

Therefore, by determining the first sleep feature of the subject based on the sleep data and the individual core sleep period, determining the second sleep feature of the subject based on the sleep data and the collective core sleep period; and determining the sleep feature data based on the first sleep feature as well as the second sleep feature, the sleep feature data of the subject can be accurately determined while taking into account individual factors of the subject.

Figure 4:
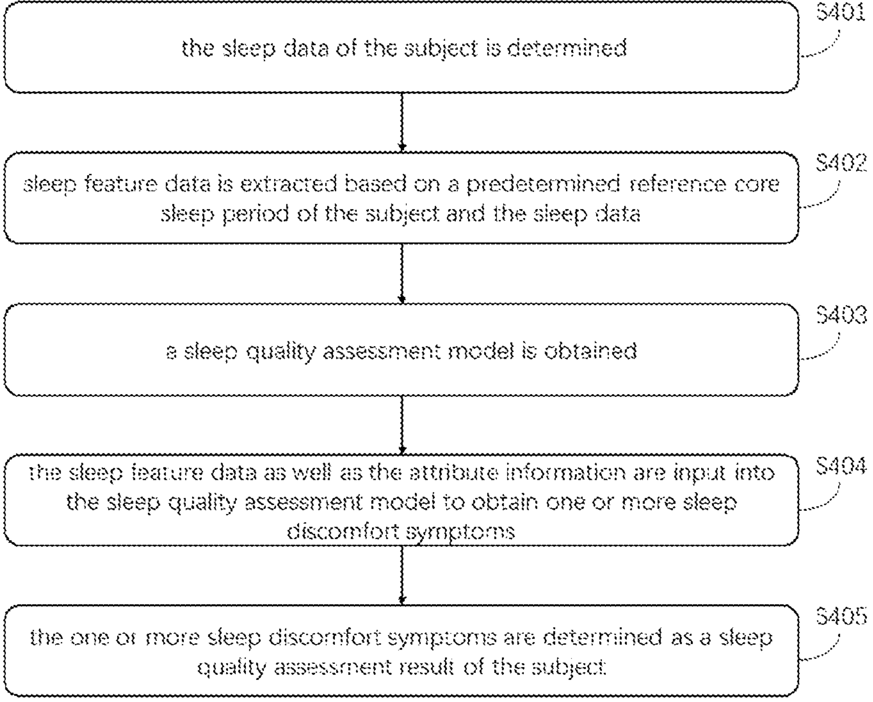
FIG. 4 is a schematic diagram of the method for sleep quality assessment according to some other implementations of the present disclosure.

In order to more accurately assess the sleep quality of the subject, as shown in FIG. 4, the method for sleep quality assessment according to some other implementations of the present disclosure is illustrated. In implementations of the present disclosure, a quality assessment model may be used to assess the sleep quality of the subject based on the sleep feature data and attribute information of the subject. The implementation shown in FIG. 4 includes the following procedures.

At S401, sleep data of the subject is determined.

At S402, sleep feature data is extracted based on a predetermined reference core sleep period of the subject and the sleep data.

At S403, a sleep quality assessment model is obtained.

Neural network models perform more prominently in cases of complex input-output relationships and an adequate amount of labeled training samples. However, recurrent neural networks are black-box models, making it difficult to explain why a pre-trained neural network makes specific decisions. On the contrary, tree models offer good interpretability. Therefore, the present disclosure employs a pre-trained neural network as a teacher model to train a tree model.

Optionally, training data is acquired, where the training data includes a predefined number of sleep feature samples. Sleep discomfort symptom samples corresponding to the sleep feature samples are determined based on the pre-trained neural network model and the predetermined number of sleep feature samples. The initial tree model is then trained using the sleep feature samples and their corresponding sleep discomfort symptom samples, resulting in a trained tree model. The trained tree model is used as the sleep quality assessment model.

Figure 5:
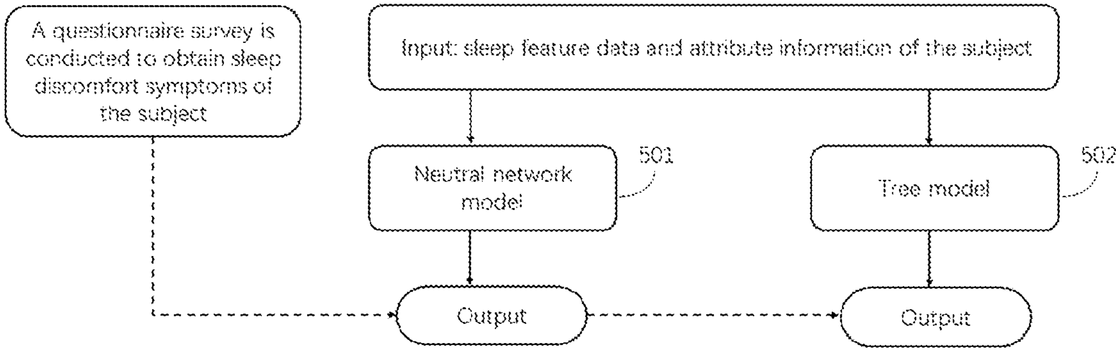
FIG. 5 is a schematic diagram of a tree model training procedure according to some implementations of the present disclosure.

As shown in FIG. 5, the sleep feature samples and attribute information may be used as inputs to the neural network model, and the neural network model is trained to obtain a pre-trained neural network model, such that outputs of the neural network model matches the sleep discomfort symptoms obtained from a questionnaire survey. The sleep discomfort symptoms output by the pre-trained neural network model 501 are used as the sleep discomfort symptom samples corresponding to the sleep feature samples. The sleep discomfort symptoms obtained by the questionnaire survey may include at least one of the following symptoms: easy awakening, early waking, insomnia, vivid dreams, feeling tired upon waking, nocturia, difficulty falling asleep at night, headache or dizziness upon waking, daytime sleepiness, difficulty falling back asleep after waking up, difficulty falling asleep again after early waking, woken up with a headache and dizziness in the morning, or frequent snoring-induced awakenings during sleep. The attribute information may include at least one of a gender, age, height, or weight. In some implementations of the present disclosure, a loss function is constructed using the sleep discomfort symptoms output from the neural network (e.g., recurrent neural network) model and the sleep discomfort symptoms obtained from the questionnaire survey, which may be expressed as the following formula:

$$\text{Loss} = L2(Y, Z) + (1 - \text{Corr}(Y, Z))^2 \tag{1}$$

$$\text{Corr}(Y, Z) = \sum (y_i - \mu_y)(z_i - \mu_z) / (\sigma_y \sigma_z) \tag{2}$$

where $Y=\{y_i\}$, $Z=\{z_i\}$, $y_i$ and $z_i$ represent the sleep discomfort symptoms obtained from the questionnaire survey and the sleep discomfort symptoms output by the neural network model, respectively.

Further, the sleep feature samples and attribute information are used as inputs to the tree model 502, and the tree model 502 is trained such that the output of the tree model matches the sleep discomfort symptom samples corresponding to the sleep feature samples obtained from the pre-trained neural network model 501, which may be expressed by the following formula:

$$\text{Loss} = L2(Y, Z) + (1 - \text{Corr}(Y, Z))^2 \quad (3)$$

$$\text{Corr}(Y, Z) = \sum (y_i - \mu_y)(z_i - \mu_z) / (\sigma_y \sigma_z) \quad (4)$$

where $Y=\{y_i\}$, $Z=\{z_i\}$, $y_i$ and $z_i$ represent the sample sleep symptoms corresponding to the sleep feature samples output by the pre-trained neural network and the sleep symptoms output by the tree model, respectively. $\mu_y$ and $\mu_z$ are respectively the means of Y and Z, $\sigma_y$ and $\sigma_z$ are the standard deviations of Y and Z.

Further, the trained tree model is used as the sleep quality assessment model.

At S404, the sleep feature data as well as the attribute information are input into the sleep quality assessment model to obtain one or more sleep discomfort symptoms.

In some implementations of the present disclosure, the sleep feature data as well as the attribute information are input into the sleep quality assessment model, and the sleep quality assessment model can output one or more sleep discomfort symptoms.

At S405, the one or more sleep discomfort symptoms are determined as a sleep quality assessment result of the subject.

Furthermore, the sleep discomfort symptoms are taken as the sleep quality assessment result of the subject.

S401 and S402 can be implemented in any way as described in various implementations disclosed in this specification, and the present disclosure are not limited thereto and will not be repeated further.

Therefore, by obtaining the sleep quality assessment model, inputting the sleep feature data and attribute information into the sleep quality assessment model to obtain one or more sleep discomfort symptoms, and determining the sleep discomfort symptoms as the sleep quality assessment result of the subject, the sleep quality of the subject can be assessed more accurately by adopting the sleep quality assessment model based on the sleep feature data and attribute information of the subject.

In the method for sleep quality assessment method provided in the implementations of the present disclosure, by determining the sleep data of the subject, extracting one or more sleep feature data based on a reference core sleep period of the subject and the sleep data of the subject, and evaluating the sleep quality of the subject based on the sleep feature data, the method evaluates the sleep quality of the subject based on the sleep feature data extracted according to the reference core sleep period and the sleep data of the subject, and the method takes into account individual factors of the subject during extraction of the sleep feature data, thereby providing a more accurate evaluation of the sleep quality of the subject.

To implement the above-mentioned implementations, the present disclosure also provides a method for in-bed status monitoring based on wearable devices.

Figure 6:
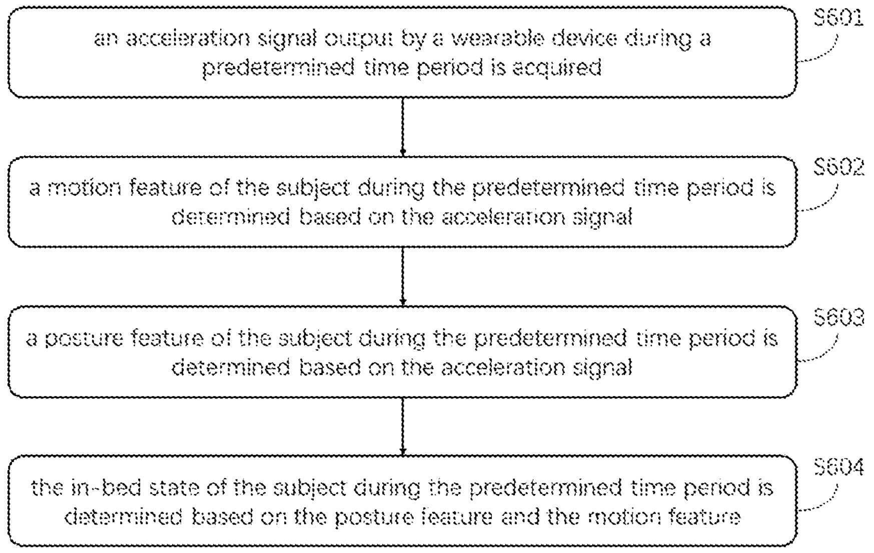
FIG. 6 is a schematic diagram of a method for in-bed state monitoring according to some implementations of the present disclosure.

FIG. 6 is a schematic diagram of the method for in-bed state monitoring according to some implementations of the present disclosure. The method for in-bed state monitoring based on wearable devices in the implementations of the present disclosure can be applied to the apparatus for in-bed state monitoring based on wearable devices in the implementations of the present disclosure, and the apparatus can be configured within electronic devices. The electronic devices can be a mobile terminal, such as a smartphone, a tablet, a personal digital assistant or other hardware devices with various operating systems.

As shown in FIG. 6, the method for in-bed state monitoring based on wearable devices may include the following procedures.

At S601, an acceleration signal output by a wearable device during a predetermined time period is acquired.

In order to accurately analyze the in-bed status of a subject, the present disclosure utilizes the wearable devices that are portable and suitable for various daily scenarios to monitor the in-bed status of subjects. When a user is wearing the wearable device, one or more sensors in the wearable device can provide a direct reflection of the user's actions. For example, the acceleration signal output from the sensor can reflect the movement of the part of the user where the wearable device is placed.

In the present disclosure, the acceleration signal may be output by a sensor in the wearable device, and the sensor can be a single-axis acceleration sensor, a dual-axis acceleration sensor, or a tri-axis acceleration sensor, and the present disclosure is not limited thereto.

In order to more accurately infer the activity state of the user, the present disclosure may use a three-axis acceleration sensor, which collects acceleration signals separately along the three axes of the spatial coordinate system, resulting in more reliable results based on the acceleration signals. The following implementations of the present disclosure are explained with the three-axis acceleration signal as an example.

The predetermined time period may be a preset time period of an arbitrary length.

Typically, since the in-bed state of the subject is usually a continuous event, in the present disclosure, an acceleration signal within the predetermined time period is acquired. That is, the acceleration signal may be a sequence including a series of acceleration values.

At S602, a motion feature of the subject during the predetermined time period is determined based on the acceleration signal.

In the present disclosure, the acceleration signal is first analyzed to determine a motion feature of the subject within the predefined time period corresponding to the acceleration signal. The motion feature of the subject may be used for indicating the active level or the activity status of the subject. For example, if all the acceleration values in the acceleration signal are below a threshold, it can be determined that the motion feature of the subject during the predetermined time period is "no motion". For another example, if at least a part of the acceleration values in the acceleration signal are above a threshold, it can be determined that the motion feature of the subject during the predetermined time period is "motion", and so on, and the present disclosure is not limited thereto.

Optionally, if the time length corresponding to the predetermined time period is relatively long, in the present disclosure, the predetermined time period can be divided into a plurality of time windows based on a specified time length, an mean absolute deviation or one or more other statistical parameters of the accelerations corresponding to a time window is determined based on an acceleration value at each moment within the time window, and the motion feature within the predetermined time period is determined based on the mean absolute deviation or one or more other statistical parameters of each of the plurality of time windows. In some implementations, during the S102, the preset time period is divided into multiple time windows based on a specified time length, a mean absolute deviation corresponding to each time window is determined based on an acceleration value at each moment within the time window, a type label corresponding to each time window is determined based on a relationship between the mean absolute deviation corresponding to the time window and an activity threshold, where the type label is used for representing an activity state of the subject during the corresponding time window, and the motion feature of the subject within the predetermined time period is determined based on the type label of each time window within the predetermined time period.

The specified time length may be pre-set, or be determined by the wearable device based on the current time. For example, at the beginning of sleep or in the early morning, a user may have frequent movements such as turning over, while a probability of movement is lower during deep sleep, so a longer specified time length can be set for the late night period, while a shorter specified time length can be set for the early morning or the beginning of sleep.

In determining the mean absolute deviation corresponding to each time window, the apparatus may first calculate a resultant acceleration based on the tri-axial acceleration measurement values acquired by the sensor. For the sake of illustration, the present disclosure denotes the tri-axial acceleration measurement values at each moment of a time window as $acc_x$, $acc_y$ and $acc_z$.

The apparatus may calculate the resultant acceleration gacc at each moment of the time window based on the tri-axis acceleration measurement values $acc_x$, $acc_y$ and $acc_z$ using the following formula:

$$gacc = \sqrt{acc_x^2 + acc_y^2 + acc_z^2} \tag{5}$$

After obtaining the resultant acceleration at each moment of the time window, the apparatus may calculate an average value of the resultant acceleration for each time window, $mean_{gacc}$, based on the number of moments, n, included in the time window and the resultant acceleration at each moment of the time window. The formula is as follows:

$$mean_{gacc} = \frac{1}{n}\sum_{i=1}^{n} gacc_i \tag{6}$$

where the $gacc_i$ is the resultant acceleration at the $i^{th}$ moment, and i is a positive integer.

The apparatus may alternatively calculate a resultant acceleration of the current time window by computing the tri-axial acceleration measurement values of the current time window, where the resultant acceleration may be served as a window acceleration of the current time window. For instance, the tri-axis acceleration measurement values at the moments in a time window are first averaged to obtain average acceleration values in the three axes for the time window, and then the average acceleration values for the time window are utilized to obtain the resultant acceleration of the time window.

Subsequently, the apparatus may obtain one or more statistic parameters based on the average resultant acceleration for each time window. For instance, the apparatus calculates a mean absolute deviation (MAD) for each time window based on the average resultant acceleration $mean_{gacc}$ and the resultant acceleration $gacc_i$ at each moment within the time window. The formula is as follows.

$$MAD = \frac{1}{n}\sum_{i=1}^{n} |gacc_i - mean_{gacc}| \tag{7}$$

Furthermore, the apparatus may determine the type label corresponding to each time window based on the relationship between the mean absolute deviation corresponding to each time window and the activity threshold. The activity threshold may be pre-set in the wearable device. Alternatively, the activity threshold may be automatically generated by the wearable device based on historical movement information of the subject. The present disclosure is not limited thereto.

The type labels in the present disclosure may be "low activity", "moderate activity", "high activity", etc., and the present disclosure is not limited thereto. It can be understood that, the number of activity thresholds may be determined according to the number of type labels. For example, if the number of type labels corresponding to the time windows is two, namely "low activity" and "high activity", then the apparatus may set one activity threshold. Based on the relationship between the mean absolute deviation corresponding to a time window and the activity threshold, the apparatus may determine the type label of the time window with a mean absolute deviation lower than or equal to the activity threshold as "low activity", and determine the type label of the time window with a mean absolute deviation higher than the activity threshold as "high activity". The present disclosure is not limited thereto.

Alternatively, if the number of type labels corresponding to the time windows is three, namely "low activity", "moderate activity", and "high activity", then the apparatus may set two activity thresholds. In this case, the present disclosure refers to a smaller activity threshold as A and a larger activity threshold as B. Based on the relationship between the mean absolute deviation corresponding to a time window and the activity thresholds, the type label of a time window with a mean absolute deviation lower than or equal to the activity threshold A may be determined as "low activity", and the type label of a time window with a mean absolute deviation higher than the activity threshold B may be labeled as "high activity", and the type label of a time window with a mean absolute deviation higher than the activity threshold A and lower than or equal to the activity threshold B may be determined as "moderate activity". The present disclosure is not limited thereto.

In the present disclosure, in order to facilitate the wearable device to statistically analyze the type labels of respective time windows in a consecutive period of time, different feature values can be used to characterize different type labels. For example, a feature value corresponding to "low activity" is 0, a feature value corresponding to "moderate activity" is 1, and a feature value corresponding to "high activity" is 2.

Accordingly, after determining the type label, i.e., the feature value, for each time window, the feature values corresponding to respective time windows may be merged, such as, for example, by arranging, or by weighted summation or the like, so as to determine the motion feature of the subject during the predetermined time period. For example, if the predetermined time period is divided into a total of 5 time windows, and the feature values corresponding to these 5 time windows are sequentially 0, 0, 1, 0 and 0, then the motion feature corresponding to the predetermined time period may be represented by arranging these feature values in a sequence to form a feature vector, i.e., [0, 0, 1, 0, 0]. Alternatively, the plurality of feature values may be merged by weighted summation or the like to determine the motion feature corresponding to the consecutive time period. The present disclosure is not limited thereto.

At S603, a posture feature of the subject during the predetermined time period is determined based on the acceleration signal.

In the present disclosure, the acceleration signal may first be analyzed to determine a posture feature of the subject during the predetermined time period corresponding to the acceleration signal. For example, if each of the acceleration values in the acceleration signal is less than a threshold, it is determined that the posture feature of the subject in the predetermined time period is a lying posture. For another example, if each of the acceleration values in the acceleration signal is greater than a threshold, it is determined that the posture feature of the subject in the predetermined time period is a sitting posture or a standing posture, and so on. No limitation is imposed in the present disclosure. In one example, a posture feature of the wearable device or a posture feature of a part of the subject wearing the wearable device is first determined based on the acceleration signal, and the posture feature of the subject is determined based on the posture feature of the wearable device or the posture feature of a part of the subject wearing the wearable device.

Optionally, if the time length of the predetermined time period is relatively long, in the present disclosure, the predetermined time period may be divided into a plurality of time windows based on a specified time length, a window acceleration corresponding to each time window is determined, and the posture feature within the predetermined time period is determined based on the window acceleration corresponding to each time window. In some implementations, in implementing the above S603, at least one time window is chosen from the plurality of time windows based on the window acceleration of each time window, where the window acceleration of the at least one time window is within a specified range. The window acceleration at the at least one time window may be stable, or the window acceleration at the at least one time window is close to the gravitational acceleration, it indicates that the wearable device is stable and almost stay still in the at least one time window. In this case, the apparatus can determine the posture feature according to the accelerations within the at least one time window. In some implementations, an acceleration vector corresponding to each of the at least one time window is determined, and at least one angle from the acceleration vector to one or more axes are determined, which can be served as part of the posture feature, or be utilized to calculate the posture feature. For instance, if the window acceleration corresponding to any one of the time windows is within a specified range, an acceleration vector corresponding to the time window is determined, a distance from each acceleration vector to a specified spherical region is determined, and the posture feature of the subject during the predetermined time period is determined based on a plurality of the distances.

For the specific implementation of determining the window acceleration, reference can be made to the detailed description of the above S102, which will not be repeated herein.

In the case where the window acceleration corresponding to a time window is within a specified range, it indicates that the apparatus may determine an acceleration vector corresponding to the time window.

Optionally, the specified range in the present disclosure may be close to the gravitational acceleration, such as, 1 g±0.1 g, 1 g±0.2 g, 1 g±0.5 g, or the like, and no limitation is set hereto, where g represents the gravitational acceleration.

Specifically, if the window acceleration corresponding to a time window is within a specified range, it indicates that the acceleration vector is stable. The apparatus may first obtain the window acceleration of the time window, and normalize the tri-axis acceleration values based on the window acceleration, so as to obtain a unit vector of the current window in the direction of the three axes.

For example, if the current window acceleration is gacc, the acceleration measurement values along the three axes are $acc_x$, $acc_y$ and $acc_z$, respectively, the acceleration measurement values along the three axes are normalized based on the window acceleration, i.e., the three components of the tri-axis acceleration measurement values in the three-dimensional Cartesian coordinate system, namely $u_x$, $u_y$ and $u_z$, are computed. The formula is as follows:

$$u_x = \frac{acc_x}{gacc} \tag{8}$$

$$u_y = \frac{acc_y}{gacc} \tag{9}$$

$$u_z = \frac{acc_z}{gacc} \tag{10}$$

Further, based on $u_x$, $u_y$ and $u_z$, an angle between the acceleration vector and the x-axis, $u_{long}$, and an angle between the acceleration vector and the z-axis, $u_{la}$, are obtained. In the present disclosure, toon g is served as the longitude, and $u_{la}$ is served as the latitude. A specific calculation process is as follows:

$$\text{If } u_x < 0 \text{ and } u_y > 0\text{, then } u_{long} = \text{atan}(u_y) + pi$$

$$\text{if } u_x < 0 \text{ and } u_y \le 0\text{, then } u_{long} = \text{atan}(u_y / u_x) + pi;$$

$$\text{if } u_x = 0\text{, then } u_{long} = \text{atan}(u_y / u_x);$$

$$\text{if } u_x > 0\text{, then } u_{long} = \text{atan}(u_y / u_x)\text{; and}$$

$$u_{la} = \text{asin}(u_z).$$

In this way, the apparatus can determine a spherical distance between the vector of the current time window and a labeled regional point, namely Dis, based on a spherical distance formula, and the formula is as follows:

$$Dis = \text{acos}(\cos(u_{la}) * \cos(i_{la}) * \cos(u_{long} - i_{long}) + \sin(u_{la}) * \sin(i_{la})) \tag{11}$$

where the longitude $i_{long}$ is an angle between a vector formed by connecting from the labeled reference point to the origin of the spherical coordinate system and the x-axis, and the latitude ha is an angle between the vector and the z-axis. The longitude $u_{long}$ is an angle between the acceleration vector and the x-axis, and the latitude $u_{la}$ is an angle between the acceleration vector and the z-axis.

The regional point may be any point in a specified spherical region, or be a specified point, which is not limited by the present disclosure.

For example, if the predetermined time period is divided into five time windows, each of which corresponds to a distance, the apparatus may perform a direct summation on the five distances or perform a weighted summation based on the weights of the five distances, and the apparatus may use a final sum as the posture feature, which is not limited by the present disclosure.

Alternatively, in the present disclosure, a direct vector summation of the window accelerations corresponding to the five time windows is performed to obtain a sum vector. Subsequently, a spherical distance between the sum vector and any point in a specified spherical region is determined as the posture feature, which is not limited by the present disclosure.

At S604, the in-bed state of the subject during the predetermined time period is determined based on the posture feature and the motion feature.

The apparatus may determine the in-bed state of the subject during the predetermined time period based on the posture feature and the motion feature of the subject, which may be "out of bed", "suspected to be out of bed", "not out of bed", etc., and the present disclosure is not limited thereto. Since the apparatus takes into account the gesture feature and motion feature, the apparatus can determine the in-bed state of the subject during the predetermined time period from two perspectives, thereby allowing for more accurate calculation of the sleep time, which not only expands the applications of the wearable device, but also makes the determination result of in-bed state more accurate and reliable.

In the implementations of the present disclosure, the wearable device first acquires an acceleration signal output by a sensor during a preset time period, determines a motion feature of the subject during the preset time period based on the acceleration signal, determines a posture feature of the subject during the preset time period based on the acceleration signal, and finally determines the in-bed status of the subject during the preset time period based on both the motion feature and the posture feature. As a result, by integrating both motion and posture features to determine the in-bed status of the subject, the accuracy and reliability of the monitoring results are improved.

Figure 7:
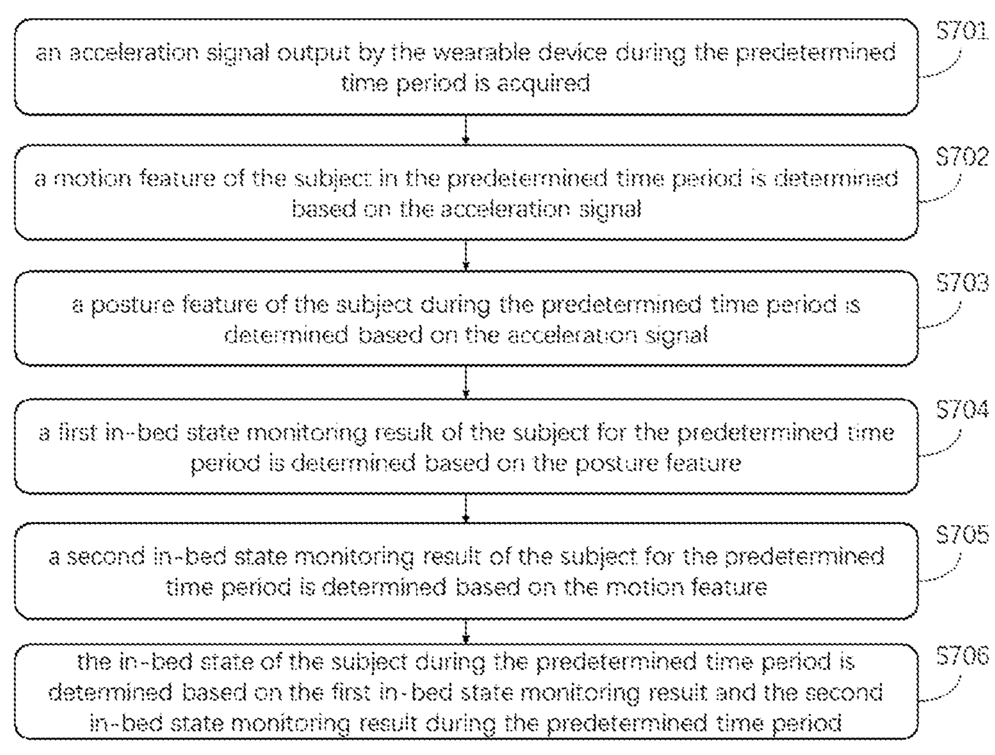
FIG. 7 is a schematic diagram of the method for in-bed state monitoring according to some other implementations of the present disclosure.

In order to realize the above implementations, the present disclosure provides another method for in-bed state monitoring based on a wearable device. FIG. 7 illustrates the method in an implementation of the present disclosure.

As shown in FIG. 7, the method for in-bed state monitoring based on the wearable device may include the following procedures.

At S701, an acceleration signal output by the wearable device during the predetermined time period is acquired.

At S702, a motion feature of the subject in the predetermined time period is determined based on the acceleration signal.

In determining the motion feature of the subject in the predetermined time period based on the acceleration signal, the apparatus needs to divide the predetermined time period into a plurality of time windows based on a specified time length, and determine a type label for each time window. The above S102 can be referred to for the specific implementations.

Optionally, the apparatus may determine a number of each type of window within the predetermined time period based on a type label of each time window within the predetermined time period, and subsequently, the apparatus may determine the motion feature in the predetermined time period based on the number of each type of window within the predetermined time period.

For example, if there are N time windows in the preset time period, and there are three type labels corresponding to the time windows, which are "low activity", "moderate activity" and "high activity", the apparatus can separately count the number of windows corresponding to these three type labels as $count_{low}$, $count_{mid}$, and $count_{high}$, where $count_{low}+count_{mid}+count_{high}=N$.

Afterwards, the number of each type label corresponding to the multiple time windows contained within the consecutive time period is used to characterize the motion feature of the predetermined time period, such as [$count_{low}$, $count_{mid}$, and $count_{high}$], which is not limited by the present disclosure.

Furthermore, the apparatus may determine a time window type sequence of the predetermined time period based on the type labels of the respective time windows within the predetermined time period.

For example, if there are five time windows in the predetermined time period, the apparatus may obtain the time window type sequence of the predetermined time period by individually determining the type label of each of the five time windows. For example, if the type labels of the five time windows are, in chronological order, "low activity", "low activity", "low activity", "high activity" and "high activity". If the type label "low activity" is labeled as M and the type label "high activity" is labeled as N, then the time window type sequence is "M, M, M, N, N".

Furthermore, after determining the time window type sequence, the apparatus may determine the number of each type of time window within the predetermined time period. For instance, the apparatus may determine from "M, M, M, N, N" that, there are three time windows of the type of "low activity" and two time windows of the type of "high activity", and the present disclosure is not limited thereto. In addition, if the feature value of the time window corresponding to M is assigned to be 1, and the feature value of the time window corresponding to N is assigned to be 2, then the apparatus can determine a feature vector [1, 1, 1, 2, 2] based on the time window type sequence "M, M, M, N, N", and thus the apparatus can use the feature vector as the motion feature. The disclosure does not impose specific limitations hereto.

After determining the type label corresponding to each time window based on the acceleration signal, the apparatus may determine an activity change point within the predetermined time period based on the type labels corresponding to the time windows. The activity change point may be used to determine a motion feature which is a time interval, and accordingly, the present disclosure may update the motion feature according to the activity change point.

The S702 mentioned above may further include: determining a moment corresponding to an activity change point in the predetermined time period based on the type labels corresponding to each time window; determining a time interval between each time window and an adjacent previous activity change point; and updating or determining the motion feature of the subject within the predetermined time period based on the time interval corresponding to each time window.

The activity change point may be an intermediate moment when a type label of a time window changes from one to another. For example, if a predetermined time period is divided into five time windows, where the type labels corresponding to the first three time windows are all "low activity", and the type labels corresponding to the last two time windows are all "moderate activity", then the apparatus may take the moments between the time window of "low activity" and the time window of "moderate activity" as the activity change point.

In the present disclosure, a time point when the time window changes from "low activity" to "moderate activity" can be taken as a moderate activity change point, and a time point when the time window changes from "moderate activity" to "high activity" can be taken as a high activity change point, and the present disclosure is not limited thereto.

It is to be understood that, if there is more than one activity change point in a consecutive time period, then there are corresponding time intervals. The apparatus may determine a time interval between each time window and a previous activity change point, e.g. a time interval between the current time window and the last high activity change point, $CP_{high}$, a time interval between the current time window and the last medium activity change point, $CP_{mid}$, or a time interval between the current time window and the last neighboring activity change point of any type, which is not limited in the present disclosure. The apparatus may use the time interval as a motion feature for determining the in-bed state of the subject.

Furthermore, the apparatus may update the motion feature of the subject in the predetermined time period according to the time interval corresponding to each time window. It can be understood that, in the present disclosure, after obtaining the time intervals between the respective time windows of the current predetermined time period and the adjacent previous activity change point, the time interval served as a motion feature is determined. The apparatus may then re-determine or supplement the motion feature of the subject in the preset time period, which is not limited by the present disclosure.

At S703, a posture feature of the subject during the predetermined time period is determined based on the acceleration signal.

If the window acceleration corresponding to a time window is within a specified range, in the present disclosure, the posture feature may be determined based on the specific implementation of above-mentioned S603, and if the window acceleration corresponding to a time window is not within the specified range, the apparatus may determine the posture feature of the subject during the preset time period based on the window acceleration corresponding to the remaining time windows within the predetermined time period.

It can be appreciated that, if the window acceleration corresponding to a time window is not within the specified range, then the apparatus may determine the posture feature with the window acceleration corresponding to the remaining time windows. For example, if there are currently a total of five time windows, and it can be determined that the window acceleration of the second time window exceeds the specified range, then the apparatus can calculate the window acceleration of the remaining four time windows, and obtain a sum vector by summing the vectors of window acceleration of the four time windows for example. Furthermore, a spherical distance between the sum vector and any point within a specified spherical region is calculated with reference to the above S603 as a posture feature, which is not limited by the present disclosure. Alternatively, in the present disclosure, the spherical distances between the window acceleration of the remaining four time windows and any point in the specified spherical region may be summed either by a simple summation or by a weight-based summation, and the apparatus may then use the resulting sum as the posture feature, which is not limited by the present disclosure.

At S704, a first in-bed state monitoring result of the subject for the predetermined time period is determined based on the posture feature.

Optionally, in determining the first in-bed state monitoring result, the apparatus may compare the feature value corresponding to the posture feature of the predetermined time period with a predetermined threshold using a threshold comparison method. There can be one or more preset thresholds, which is not limited by the present disclosure. If there is only one preset threshold, then if the current feature value is higher than the threshold, the first in-bed state monitoring result of the subject in the preset time period can be determined to be an out-of-bed state, and if the current feature value is lower than the threshold, the first in-bed state monitoring result of the subject in the preset time period can be determined to be an in-bed state. The present disclosure is not limited thereto.

At S705, a second in-bed state monitoring result of the subject for the predetermined time period is determined based on the motion feature.

Optionally, in determining the second in-bed state monitoring result, the apparatus may input respective motion features into the pre-trained decision tree model to obtain an output result of the second in-bed state monitoring result. The motion features may include a number of time windows corresponding to each type label within the predetermined time period, as well as a time interval between each time window in the predetermined time period and an adjacent previous activity change point, etc., which is not limited by the present disclosure.

Alternatively, a template matching method may be used. For example, a template library for in-bed status is established in advance, where the template library contains feature vectors of various samples. The apparatus inputs the vector of the motion feature of the subject, obtains a matching degree between the motion feature vector of the subject and the feature vectors of various samples in the template library, so as to further determine whether the second in-bed state monitoring result is "out of bed", "suspected to be out of bed", or "not out of bed", which is not limited by the present disclosure.

At S706, the in-bed state of the subject during the predetermined time period is determined based on the first in-bed state monitoring result and the second in-bed state monitoring result during the predetermined time period.

Optionally, in the case where the first in-bed state monitoring result and the second in-bed state monitoring result are the same, the apparatus determines that the in-bed state of the subject during the predetermined time period to be either the first in-bed state monitoring result or the second in-bed state monitoring result. It can be understood that, if the first in-bed state monitoring result is the same as the second in-bed state monitoring result, for example, both the first in-bed state monitoring result and the second in-bed state monitoring result are "out of bed", then the apparatus can determine the in-bed state of the subject in the preset time period to be "out of bed", and the present disclosure is not limited thereto.

In addition, if the first in-bed state monitoring result and the second in-bed state monitoring result are different from each ither, and either of the first in-bed state monitoring result and the second in-bed state monitoring result is a non-in-bed state, then the apparatus may determine that the in-bed state of the subject during the predetermined time period is not in bed, which may be "out of bed" or "suspected to be out of bed", which is not limited by the present disclosure.

For example, if the first in-bed state monitoring result is out of bed and the second in-bed state monitoring result is not out of bed, since the first in-bed state monitoring result is not in bed, the apparatus may determine that the in-bed state of the subject within the predetermined time period is not in bed. Alternatively, if the second in-bed state monitoring result is suspected to be out of bed, the apparatus may determine that the in-bed state of the subject during the preset time period is not in bed, which is not limited by the present disclosure.

In the implementations of the present disclosure, the wearable device first acquires the acceleration signal outputted by the sensor during a preset time period, determines the motion feature of the subject during the preset time period based on the acceleration signal, determines the posture feature of the subject during the preset time period based on the acceleration signal, determines the first in-bed state monitoring result of the subject during the preset time period based on the posture feature, determines the second in-bed state monitoring result of the subject during the preset time period based on the motion features, and finally determines the in-bed state of the subject during the preset time period based on the first in-bed state monitoring result and the second in-bed state monitoring result during the preset time period. By separately determining the in-bed state within the preset time period based on the motion feature and the posture feature, the accuracy and reliability of the monitoring results are improved.

Figure 8:
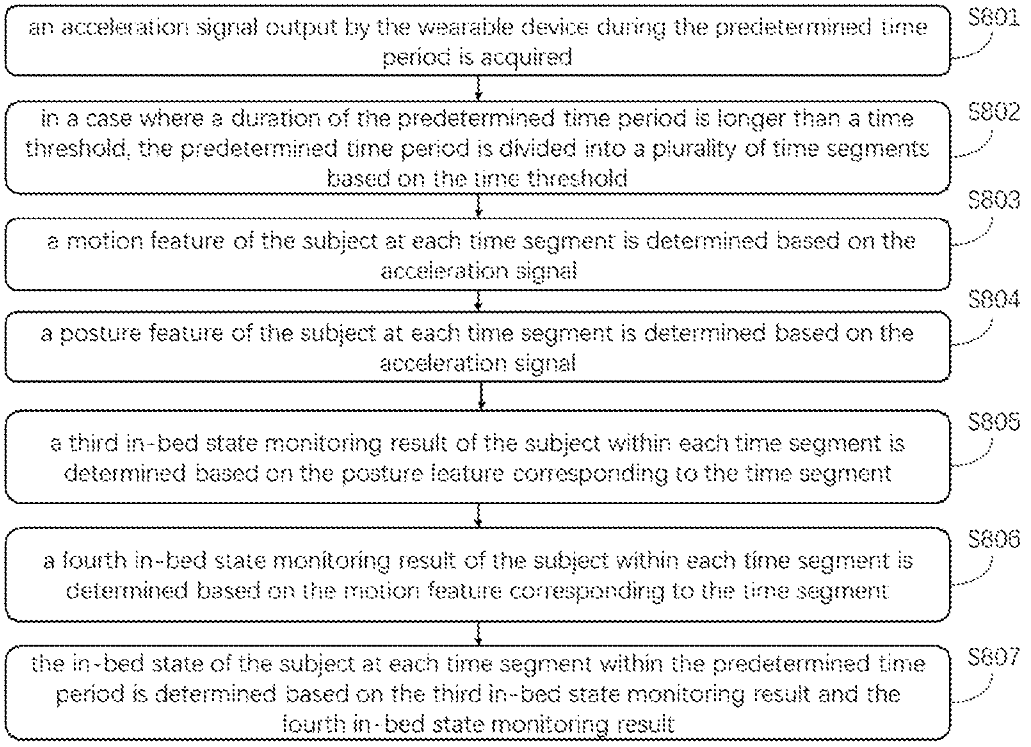
FIG. 8 is a schematic diagram of the method for in-bed state monitoring according to some other implementations of the present disclosure.

In order to implement the above-described implementations, the present disclosure provides another method for in-bed status monitoring based on the wearable device, which is illustrated in FIG. 8.

As shown in FIG. 8, the method for in-bed state monitoring based on the wearable device may include the following procedures.

At S801, an acceleration signal output by the wearable device during the predetermined time period is acquired.

At S802, in a case where a duration of the predetermined time period is longer than a time threshold, the predetermined time period is divided into a plurality of time segments based on the time threshold.

Specifically, if the duration of the predetermined time segment is longer than the time threshold, it indicates that the predetermined time segment is too long. In order to more accurately determine the in-bed state of the subject, in the present disclosure, the predetermined time period is divided into a plurality of time segments based on the time threshold, where the plurality of time segments may be equally divided or unequally divided, which is not limited by the present disclosure.

At S803, a motion feature of the subject at each time segment is determined based on the acceleration signal.

In the present disclosure, the acceleration signal may first be analyzed to determine a motion feature of the subject within each time segment corresponding to the acceleration signal. For example, if an acceleration value in the acceleration signal at a time segment is less than a threshold, it is determined that the motion feature of the subject within the time segment is: no motion. For another example, if an acceleration value in the acceleration signal at a time segment is greater than a threshold, it is determined that the motion feature of the subject within the time segment is: motion, and so on, which is not limited by the present disclosure.

At S804, a posture feature of the subject at each time segment is determined based on the acceleration signal.

In the present disclosure, based on the window acceleration corresponding to each time segment, a distance between the window acceleration and a specified spherical region may be determined, and a posture feature within the predetermined time period is then determined based on the distance between the window acceleration and the specified spherical region corresponding to each time segment. For example, if the distance between the window acceleration and the specified spherical region at a time segment is less than a threshold, then the posture feature of the subject within the time segment is determined as: a lying posture. For another example, if the distance between the window acceleration and the specified spherical region at a time segment is greater than a threshold, then the posture feature of the subject within the time segment is determined as: a sitting posture or a standing posture, etc., which is not limited by the present disclosure.

At S805, a third in-bed state monitoring result of the subject within each time segment is determined based on the posture feature corresponding to the time segment.

In the present disclosure, the apparatus can calculate an acceleration vector for each moment by determining the acceleration at respective moments corresponding to each time segment. A distance between each acceleration vector and the specified spherical region is ten calculated based on the acceleration vectors at the respective moments, the distances for the respective moments are summed or weighted summed, and finally the result is used as the posture feature. The apparatus may compare the feature value corresponding to the posture feature of the preset time period with the preset threshold using a threshold comparison method, so as to determine the third in-bed state monitoring result, S704 can be referred to for details, which will not be repeated herein in the present disclosure.

At S806, a fourth in-bed state monitoring result of the subject within each time segment is determined based on the motion feature corresponding to the time segment.

In the present disclosure, the above mentioned S205 for the preset time period can be referred to for the specific implementation for determining the in-bed state of the subject by the apparatus based on the motion feature corresponding to each time segment, which is not repeated herein.

At S807, the in-bed state of the subject at each time segment within the predetermined time period is determined based on the third in-bed state monitoring result and the fourth in-bed state monitoring result corresponding to each of the plurality of time segments within the predetermined time period.

Optionally, since it takes time for the subject to transition from one in-bed state to another, in this disclosure, if there are other types of in-bed states between two identical in-bed states and the time interval between these two identical in-bed states is relatively short, the other in-bed states located between these two identical in-bed states can be converted to the same in-bed state as these two identical in-bed states.

In the case where at least one of the in-bed states corresponding to the $i^{th}$ time segment is out of bed, at least one of the in-bed states corresponding to the $(i+m)^{th}$ time segment is out of bed, and m is less than a specified value, the apparatus may determine that the in-bed state corresponding to each of the time segments between the $i^{th}$ time segment and the $(i+m)^{th}$ time segment are all out of bed, where both i and m are positive integers.

It can be understood that, if an interval between two time segments is less than a specified value, and at least one of the in-bed states corresponding to both time segments is "out of bed", then the in-bed states of the two time segments as well as each of the time segments in between the two time segments may be considered to be out of bed.

For example, if the apparatus divides a consecutive time period into six time segments with corresponding serial numbers of 1, 2, 3, 4, 5, and 6, the apparatus determines that the in-bed states of both time segment 4 and the time segment 6 are out of bed according to the acceleration information corresponding to each time segment, and the difference "1" between the two time segments is less than a specified value "2", then the apparatus may consider the in-bed state of the time segment 4, the time segment 6 as well as the time segment 5 in between to be out of bed, and the present disclosure is not limited thereto.

Optionally, considering that a transition from the in-bed state of "out of bed" to "in bed" or vice versa may be recognized as the in-bed state of "suspected to be out of bed", and that sleep quality is determined based on the duration in bed and total sleep duration, in the present disclosure, in order to further improve the accuracy of sleep quality determined by the wearable device, the in-bed states of "suspected to be out of bed" adjacent to the in-bed state of "out of bed" are uniformly converted to the in-bed state of "out of bed".

In a case where at least one of the in-bed states corresponding to the $j^{th}$ time segment is out of bed, and at least one of the in-bed states corresponding to other time segments adjacent to the $j^{th}$ time segment is suspected to be out of bed, the apparatus may determine that the in-bed state corresponding to other time segments adjacent to the $j^{th}$ time segment to be out of bed, where j is a positive integer.

It can be understood that, if at least one of the third in-bed state monitoring result and the fourth in-bed state monitoring result corresponding to the $j^{th}$ time segment is out of bed, and at least one in-bed state corresponding to the $(j-1)^{th}$ time segment adjacent to the $j^{th}$ time segment is suspected to be out of bed, the apparatus may consider the in-bed state of the $(j-1)^{th}$ time segment adjacent to the $j^{th}$ time segment to be out of bed.

By determining the in-bed status of the current subject through the fusion of the above results can enhance the stability and reliability of in-bed status monitoring, resulting in more stable outcomes.

In the implementations of the present disclosure, by first dividing the predetermined time period into a plurality of time segments based on the time threshold, determining, based on the acceleration signal, a motion feature and a posture feature of the subject for each of the time segments, and subsequently determining the third in-bed state monitoring result of the subject for each of the time segments based on the posture features corresponding to the respective time segments, determining the fourth in-bed state monitoring result of the subject for each of the time segments based on the motion features corresponding to the respective time segments, and finally determining the in-bed state of the subject in each of the time segments within the predetermined time period based on the third in-bed state monitoring results and the fourth in-bed state monitoring results corresponding to the respective time segments within the predetermined time period. Thus, by determining the in-bed state of the subject in the predetermined time period based on the motion features and the posture features of the respective time segments, the accuracy and reliability of monitoring the in-bed state are improved.

It should be noted that, the above implementations of the method for in-bed state monitoring based on the wearable device may be performed alone or in combination with the implementations of the method for sleep quality assessment. In some implementations, the in-bed state of the subject during the predetermined time period is taken as a trigger condition for physiological data measurement in sleep monitoring. In some implementations, the in-bed state of the subject during the predetermined time period is utilized to determine one or more sleep parameters, such as in-bed time, sleep efficiency, time to fall asleep, sleep latency, and so on, or the in-bed state of the subject is used for sleep quality assessment.

In some implementations, at least one sleep monitoring parameter of the subject can be derived based on the in-bed status of the subject during the predetermined time period and the sleep data of the subject. The sleep monitoring parameter may be at least a part of a result of the sleep quality assessment. The sleep monitoring parameter may be provided to the subject through various forms such as sound, visual, tactile or the like, or the sleep monitoring parameter may be utilized to derive other sleep monitoring parameters. For example, based on the sleep data, the time fall to asleep and wake-up time of the subject are determined, and a time interval between the last out-of-bed event before falling asleep and the first out-of-bed event after awakening can be determined as the in-bed time of the subject. As another example, a total sleep time of the subject is determined based on the sleep data, and the ratio of the total sleep time to the in-bed time of the subject is determined as sleep efficiency of the subject. The present disclosure is not limited thereto.

In some implementations, one or more sleep suggestions are generated and provided based on the in-bed status of the subject and the sleep data, where the sleep suggestions are intended to address sleep discomfort symptoms of the subject or improve the sleep quality of the subject. For instance, the sleep suggestions may include at least one of suggested time to go to bed, suggested activities in bed, suggested activities before going to bed, suggested sleep duration, suggested wakeup time, or the like.

Figure 9:
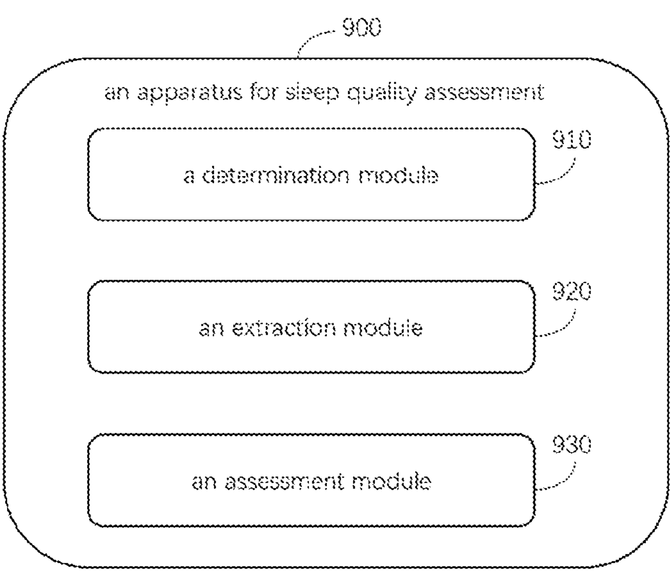
FIG. 9 is a schematic diagram of an apparatus for sleep quality assessment according to some implementations of the present disclosure.

In order to implement the above implementations of the method for sleep quality assessment, the present disclosure also provides an apparatus for sleep quality assessment. FIG. 9 illustrates a schematic diagram of the apparatus for sleep quality assessment according to some implementations of the present disclosure.

As shown in FIG. 9, the apparatus for sleep quality assessment 900 includes: a determination module 910, an extraction module 920, and an assessment module 930.

The determination module 910 is configured to determine sleep data of a subject. The extraction module 920 is configured to extract sleep feature data based on a reference core sleep period of the subject and the sleep data. The assessment module 930 is configured to evaluate sleep quality of the subject based on the sleep feature data.

In some possible implementations, the determination module 910 is configured to acquire physiological data of the subject responsive to the in-bed state of the subject within the predetermined time period being not out of bed; and perform sleep recognition on the physiological data to obtain sleep data of the subject.

In some possible implementations, the reference core sleep period includes at least one of an individual core sleep period of the subject, or a collective core sleep period of a group in an area to which the subject belongs.

In some possible implementations, the reference core sleep period includes the individual core sleep period and the collective core sleep period. Accordingly, the extraction module 920 is configured to determine a first sleep feature of the subject based on the sleep data and the individual core sleep period, determine a second sleep feature of the subject based on the sleep data and the collective core sleep period, and determine the sleep feature data based on the first sleep feature as well as the second sleep feature.

In some possible implementations, the apparatus for sleep quality assessment 900 further includes: a first acquisition module, configured to acquire attribute information of the subject, and the assessment module 930 is configured to perform the sleep quality assessment for the subject based on the sleep feature data and the attribute information.

In some possible implementations, the assessment module 930 is further configured to acquire a sleep quality assessment model, input the sleep feature data and the attribute information into the sleep quality assessment model to obtain a sleep discomfort symptom, and determine the sleep discomfort symptom as a sleep quality assessment result of the subject.

In some possible implementations, the sleep quality assessment model is a tree model. The assessment module 930 is configured to acquire train data, where the train data includes a predefined number of sleep feature samples, determine sleep discomfort symptom samples corresponding to the sample sleep feature data based on a pre-trained neural network model and the predefined number of the sleep feature samples, train an initial tree model with the sleep feature samples and the correspond sleep discomfort symptom samples to obtain a trained tree model, and take the trained tree model as the sleep quality assessment model.

In some possible implementations, the apparatus for sleep quality assessment 900 further includes: a second acquisition module, a first determination module, a second determination module, and a third determination module.

The second acquisition module is configured to obtain an acceleration signal output by the wearable device for the predetermined time period. The first determination module is configured to determine a motion feature of the subject during the predetermined time period based on the acceleration signal. The second determination module is configured to determine a posture feature of the subject during the predetermined time period based on the acceleration signal. The third determination module is configured to determine an in-bed state of the subject during the predetermined time period based on the posture feature and the motion feature.

In some possible implementations, the acceleration signal includes accelerations at respective moments. The first determination module includes a division unit, a first determination unit, a second determination unit, and a third determination unit.

The division unit is configured to divide the predetermined time period into a plurality of time windows based on a specified time length. The first determination unit is configured to determine a mean absolute deviation corresponding toing each time window based on the acceleration at each moment within the time window. The second determination unit is configured to determine a type label corresponding to each time window based on a relationship between the mean absolute deviation corresponding to the time window and an activity threshold, where the type label is used for characterize an activity state of the subject during a correspond time window. The third determination unit is configured to determine the motion feature of the subject during the predetermined time period based on the type label of each time window within the predetermined time period.

In some possible implementations, the first determination module is further configured to determine a moment corresponding to an activity change point within the predetermined time period based on the type label corresponding to each time window, determine a time interval between each time window and an adjacent previous activity change point, and update the motion feature of the subject during the predetermined time period based on the time interval corresponding to each time window.

In some possible implementations, the third determination unit is configured to determine a time window type sequence within the predetermined time period based on the type label of each time window within the predetermined time period; and/or determine a number of windows of each type within the predetermined time period based on the type label of each time window within the predetermined time period.

In some possible implementations, the acceleration signal includes accelerations at respective moments. The second determination module is configured to divide the predetermined time period into a plurality of time windows based on a specified time length, determine a window acceleration corresponding to each time window based on the acceleration at each moment within the time window, and in a case where the window acceleration corresponding to a time window is within a specified range, determine an acceleration vector corresponding to the time window, determine a distance between each the acceleration vector and a specified spherical region, and determine the posture feature of the subject during the predetermined time period based on a plurality of distances during the predetermined time period.

In some possible implementations, the second determination module is further configured to determine, in a case that the window acceleration corresponding to a time window is not within the specified range, the posture feature of the subject during the predetermined time period based on window accelerations corresponding to remain time windows within the predetermined time period.

In some possible implementations, the third determination module includes: a fourth determination unit, configured to determine a first in-bed state monitoring result of the subject during the predetermined time period based on the posture feature, a fifth determination unit, configured to determine a second in-bed state monitoring result of the subject during the predetermined time period based on the motion feature, and a sixth determination unit, configured to determine the in-bed state of the subject during the predetermined time period based on the first in-bed state monitoring result and the second in-bed state monitoring result.

In some possible implementations, the sixth determination unit is further configured to determine, in response to the first in-bed state monitoring result be different from the second in-bed state monitoring result and either of the first in-bed state monitoring result and the second in-bed state monitoring result be not in bed, the in-bed state of the subject during the predetermined time period to be not in bed.

In some possible implementations, the third determination module includes: a second division unit, configured to divide the predetermined time period into a plurality of time segments based on the time threshold, a seventh determination unit, configured to determine a third in-bed state monitoring result of the subject within each time segment based on a posture feature corresponding to the time segment, an eighth determination unit, configured to determine a fourth in-bed state monitoring result of the subject within each time segment based on the motion feature corresponding to the time segment, and a ninth determination unit, configured to determine, based on the third in-bed state monitoring result and the fourth in-bed state monitoring result corresponding to each time segment within the predetermined time segment, in-bed states of the subject corresponding to the plurality of time segments within the predetermined time period.

In some possible implementations, the ninth determination unit is configured to: in response to at least one of the third and the fourth in-bed state monitoring results corresponding to the $i^{th}$ time segment being out of bed, at least one of the third and the fourth in-bed state monitoring results corresponding to the $(i+m)^{th}$ time segment being out of bed, and m being less than a specified value, determine the in-bed state corresponding to each of the time segments between the $i^{th}$ time segment and the $(i+m)^{th}$ time segment to be out of bed, wherein both i and m are positive integers.

In some possible implementations, the ninth determination unit is further configured to: in response to at least one of the third and the fourth in-bed state monitoring results corresponding to the $j^{th}$ time segment being out of bed and at least one of the third and the fourth in-bed state monitoring results corresponding to other time segments adjacent to the $i^{th}$ time segment being suspected to be out of bed, determine the in-bed states corresponding to other time segments adjacent to the $j^{th}$ time segment being out of bed, wherein j is a positive integer.

The apparatus for sleep quality assessment in the implementations of the present disclosure, by determining the sleep data of the subject, extracting the sleep feature data based on the reference core sleep period of the subject and the sleep data, and performing sleep quality assessment based on the sleep feature data, the apparatus assesses sleep quality of the subject based on the sleep feature data extracted based on the reference core sleep period of the subject and the sleep data of the subject, and takes individual factors of the subject into account in the extraction of the sleep feature data, thereby providing a more accurate assessment of the sleep quality of the subject.

Figure 10:
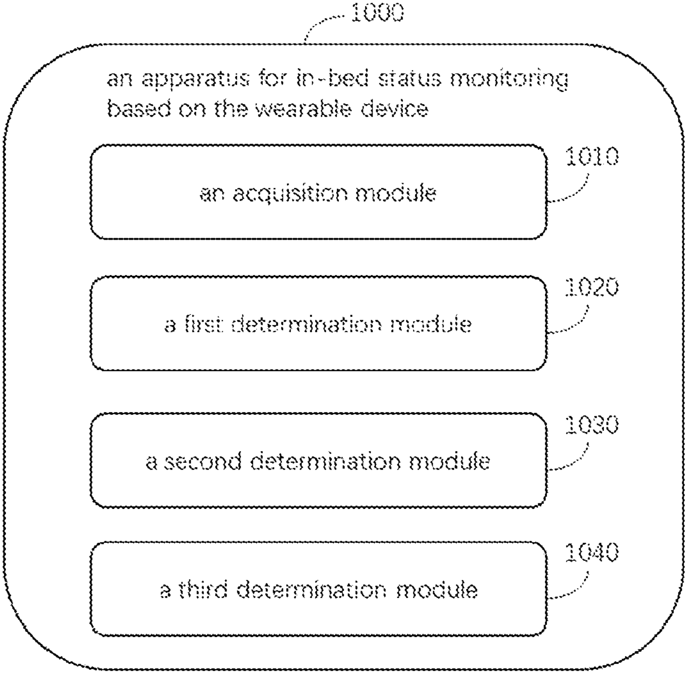
FIG. 10 is a schematic diagram of an apparatus for in-bed state monitoring according to some implementations of the present disclosure.

In order to implement the above implementations of the method for in-bed status monitoring based on the wearable device, the present disclosure also provides an apparatus for in-bed status monitoring based on the wearable device. FIG. 10 illustrates a schematic diagram of the apparatus for in-bed status monitoring according to some implementations of the present disclosure.

As shown in FIG. 10, the apparatus for in-bed status monitoring based on the wearable device 1000 includes: an acquisition module 1010, a first determination module 1020, a second determination module 1030, and a third determination module 1040.

The acquisition module 1010 is configured to acquire an acceleration signal output by the wearable device for the predetermined time period, the first determination module 1020 is configured to determine a motion feature of the subject during the predetermined time period based on the acceleration signal, the second determination module 1030 is configured to determine a posture feature of the subject during the predetermined time period based on the acceleration signal, and the third determination module 1040 is configured to determine an in-bed state of the subject during the predetermined time period based on the posture feature and the motion feature.

In some possible implementations, the acceleration signal includes accelerations at a plurality of moments. The first determination module 1020 includes a division unit, a first determination unit, a second determination unit, and a third determination unit.

The division unit is configured to divide the predetermined time period into a plurality of time windows based on a specified time length. The first determination unit is configured to determine a mean absolute deviation corresponding to each time window based on the acceleration at each of the plurality of moments within the time window. The second determination unit is configured to determine a type label corresponding to each time window based on a relationship between the mean absolute deviation corresponding to the time window and an activity threshold, where the type label is used for characterize an activity state of the subject during a correspond time window. The third determination unit is configured to determine the motion feature of the subject during the predetermined time period based on the type label of each time window within the predetermined time period.

In some possible implementations, the first determination module 1020 is further configured to determine a moment corresponding to an activity change point within the predetermined time period based on the type label corresponding to each time window, determine a time interval between each time window and an adjacent previous activity change point, and update the motion feature of the subject during the predetermined time period based on the time interval corresponding to each time window.

In some possible implementations, the third determination unit is configured to determine a time window type sequence within the predetermined time period based on the type label of each time window within the predetermined time period; and/or determine a number of windows of each type within the predetermined time period based on the type label of each time window within the predetermined time period.

In some possible implementations, the acceleration signal includes accelerations at a plurality of moments. The second determination module 1030 is configured to divide the predetermined time period into a plurality of time windows based on a specified time length, determine a window acceleration corresponding to each time window based on the acceleration at each moment within the time window, and in a case where the window acceleration corresponding to a time window is within a specified range, determine an acceleration vector corresponding to the time window, determine a distance between each the acceleration vector and a specified spherical region, and determine the posture feature of the subject during the predetermined time period based on a plurality of distances during the predetermined time period.

In some possible implementations, the second determination module 1030 is further configured to determine, in a case that the window acceleration corresponding to a time window is not within the specified range, the posture feature of the subject during the predetermined time period based on window accelerations corresponding to remain time windows within the predetermined time period.

In some possible implementations, the third determination module 1040 includes: a fourth determination unit, a fifth determination unit and a sixth determination unit. The fourth determination unit is configured to determine a first in-bed state monitoring result of the subject during the predetermined time period based on the posture feature. The fifth determination unit is configured to determine a second in-bed state monitoring result of the subject during the predetermined time period based on the motion feature. The sixth determination unit is configured to determine the in-bed state of the subject during the predetermined time period based on the first in-bed state monitoring result and the second in-bed state monitoring result.

In some possible implementations, the sixth determination unit is further configured to determine, in response to the first in-bed state monitoring result be different from the second in-bed state monitoring result and either of the first in-bed state monitoring result and the second in-bed state monitoring result be not in bed, the in-bed state of the subject during the predetermined time period to be not in bed.

In some possible implementations, the third determination module 1040 includes: a second division unit, a seventh determination unit, an eighth determination unit and a ninth determination unit.

The second division unit is configured to divide the predetermined time period into a plurality of time segments based on the time threshold. The seventh determination unit is configured to determine a third in-bed state monitoring result of the subject within each time segment based on a posture feature corresponding to the time segment. The eighth determination unit is configured to determine a fourth in-bed state monitoring result of the subject within each time segment based on the motion feature corresponding to the time segment. The ninth determination unit is configured to determine, based on the third in-bed state monitoring result and the fourth in-bed state monitoring result corresponding to each time segment within the predetermined time segment, in-bed states of the subject corresponding to the plurality of time segments within the predetermined time period.

In some possible implementations, the ninth determination unit is configured to: in response to at least one of the third and the fourth in-bed state monitoring results corresponding to the $i^{th}$ time segment being out of bed, at least one of the third and the fourth in-bed state monitoring results corresponding to the $(i+m)^{th}$ time segment being out of bed, and m being less than a specified value, determine the in-bed state corresponding to each of the time segments between the $i^{th}$ time segment and the $(i+m)^{th}$ time segment to be out of bed, wherein both i and m are positive integers.

In some possible implementations, the ninth determination unit is further configured to: in response to at least one of the third and the fourth in-bed state monitoring results corresponding to the $j^{th}$ time segment being out of bed and at least one of the third and the fourth in-bed state monitoring results corresponding to other time segments adjacent to the $j^{th}$ time segment being suspected to be out of bed, determine the in-bed states corresponding to other time segments adjacent to the $j^{th}$ time segment being out of bed, wherein j is a positive integer.

In the implementations of the present disclosure, the wearable device first acquires an acceleration signal output by a sensor during a preset time period, determines a motion feature of the subject during the preset time period based on the acceleration signal, determines a posture feature of the subject during the preset time period based on the acceleration signal, and finally determines the in-bed status of the subject during the preset time period based on both the motion feature and the posture feature. As a result, by integrating both motion and posture features to determine the in-bed status of the subject, the accuracy and reliability of the monitoring results are improved.

In order to implement the above-mentioned implementation, such as the examples shown in at least one of FIG. 1 to FIG. 8, the present disclosure further provides an electronic device including: at least one processor; and a memory communicatively coupled to the at least one processor. The memory stores instructions executable by the at least one processor, and execution of the instructions by the at least one processor causes the at least one processor to perform the method for sleep quality assessment, such as the examples shown in at least one of FIG. 1 to FIG. 8.

In order to implement the above-mentioned implementation, such as the examples shown in at least one of FIG. 1 to FIG. 8, the present disclosure further provides a wearable device including: an acceleration sensor, one or more wearable accessories, at least one processor, and a memory communicatively coupled to the at least one processor. The memory stores instructions executable by the at least one processor, and execution of the instructions by the at least one processor causes the at least one processor to perform the method for in-bed state monitoring based on the wearable device, such as the examples shown in at least one of FIG. 1 to FIG. 8. The one or more wearable accessories may include a wearable band. In some implementations, the wearable device may further include one or more physiological sensors configured to acquire physiological data of the subject.

In order to implement the above implementations, the present disclosure provides a non-transitory computer readable storage medium, having computer instructions stored thereon, where the computer instructions are configured to cause a computer to perform the method for sleep quality assessment, such as the examples shown in FIG. 1 to FIG. 5, or to perform the method for in-bed state monitoring based on the wearable device, such as the examples shown in FIG. 6 to FIG. 8.

In order to implement the above implementations, the present disclosure provides a computer program product including a computer program. The computer instructions are configured to cause a computer to perform the method for sleep quality assessment, such as the examples shown in FIG. 1 to FIG. 5, or to perform the method for in-bed state monitoring based on the wearable device, such as the examples shown in FIG. 6 to FIG. 8.

Figure 11:
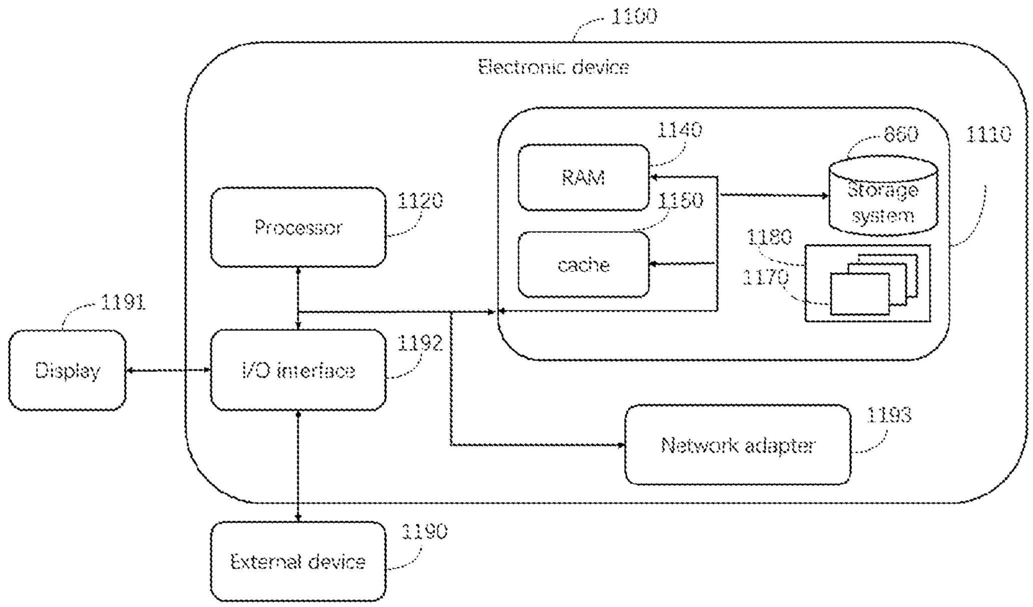
FIG. 11 is a block diagram of an electronic device for sleep quality assessment according to some implementations of the present disclosure.

FIG. 11 illustrates a schematic block diagram of an example electronic device 1100 that can be used to implement at least one implementation of the present disclosure. The electronic devices are intended to encompass various forms of digital computers, such as laptops, desktop computers, workstations, personal digital assistants, servers, blade servers, mainframe computers, and the like. The electronic device can also encompass various forms of mobile devices, such as personal digital processing, cellular phones, smart phones, wearable devices, and the like. The components shown herein, their connections and relationships, and their functionality are provided for illustration purposes and are not intended to limit the implementations of the present disclosure as described and/or claimed herein.

As shown in FIG. 11, the electronic device includes: one or more processors 1101, a memory 1102, and interfaces for connecting various components, including a high speed interface and a low speed interface. The components are connected to each other utilizing different buses and may be mounted on a common motherboard or otherwise mounted as desired. The processor can process instructions executed within the electronic device, including instructions stored in or on the memory to display graphical information of the GUI on an external input/output device, such as, for example, a display device coupled to the interface. In other implementations, multiple processors and/or multiple buses may be used in conjunction with multiple memories if desired. Similarly, a plurality of electronic devices may be connected, each providing part of the necessary operations (e.g., as an array of servers, a group of blade servers, or a multi-processor system). FIG. 11 illustrates an example with one processor 1101.

The memory 1102 is the non-transitory computer-readable storage medium provided by the present application. The memory stores instructions executable by at least one processor to cause the at least one processor to perform the method for sleep quality assessment provided by the present application.

The memory 1102, as a non-transitory computer-readable storage medium, can be used to store non-transitory software programs, non-transitory computer-executable programs, and modules such as program instructions/modules corresponding to the method for sleep quality assessment in the implementations of the present application (e.g., the determination module 910, the extraction module 920, and the assessment module 930 shown in FIG. 9). The processor 1101 executes various functional applications of the server and data processing by running the non-transitory software programs, instructions, and modules stored in the memory 1102, and realizing the method for sleep quality assessment in the above-described implementations.

The memory 1102 may include a program storage area and a data storage area. The program storage area can store an operating system and at least one application program required for functionality. The data storage area can store data created based on the use of the electronic device for sleep quality assessment and the like. Additionally, the memory 1102 may include a high-speed random access memory or a non-transitory storage device such as at least one disk storage device, flash memory device, or other non-transitory solid-state storage device. In some implementations, the memory 1102 optionally includes a storage remotely located relative to the processor 1101, and the remote storage device can be connected to the electronic device via a network. Examples of the networks include, but are not limited to, the Internet, a corporate intranet, a local area network, a mobile communications network, and combinations thereof.

The electronic device may further comprise: an input device 1103 and an output device 1104. The processor 1101, the memory 1102, the input device 1103, and the output device 1104 may be connected via a bus or otherwise, and the connection via a bus is taken as an example in FIG. 11.

The input device 1103 can receive input in the form of digital or character information and generate key signal inputs related to user settings and function control of the electronic device for sleep quality assessment. Examples of input devices include touch screens, small keyboards, mice, trackpads, touchpads, pointing sticks, one or more mouse buttons, trackballs, joysticks, and the like.

The output device 1104 includes a display device, an auxiliary lighting device (e.g., an LED), a haptic feedback device (e.g., a vibration motor) and the like. The display device may include, but is not limited to, a liquid crystal display (LCD), a light emitting diode (LED) display, and a plasma display. In some implementations, the display device may be a touch screen.

Various implementations of the systems and techniques described herein can be implemented in digital electronic circuit systems, integrated circuit systems, specialized application-specific integrated circuits (ASICs), computer hardware, firmware, software, and/or their combinations thereof. These various implementations can include implementations in one or more computer programs executable and/or interpretable on a programmable system that includes at least one programmable processor. The programmable processor can be a specialized or general-purpose programmable processor and can receive data and instructions from a storage system, at least one input device, and at least one output device, and can transmit data and instructions to the storage system, at least one input device, and at least one output device.

These computing programs (also referred to as programs, software, software applications, or code) include machine instructions for programmable processors, and can be implemented using high-level procedural and/or object-oriented programming languages and/or assembly/machine languages. As used herein, the terms “machine-readable medium” and “computer-readable medium” refer to any computer program product, device, and/or apparatus used to provide machine instructions and/or data to a programmable processor, including but not limited to disks, CDs, memory, programmable logic devices (PLDs), which receive machine instructions as machine-readable signals. The term “machine-readable signal” refers to any signal used to provide machine instructions and/or data to a programmable processor.

To facilitate interaction with users, the systems and techniques described herein can be implemented on a computer that includes a display device (e.g., a CRT or LCD monitor) for displaying information to the user, as well as a keyboard and a pointing device (e.g., a mouse or trackball) through which the user can provide input to the computer. Other types of devices may be used to provide input to the computer. Other types of devices may be used for interaction with the users. For example, the feedback provided to the user may be in any form of sensory feedback such as visual feedback, auditory feedback, or tactile feedback; and the input from the users may be received in any form including acoustic, voice, or tactile input.

The systems and techniques described herein can be implemented in a computing system that includes a back-end component such as a data server, or a computing system that includes a middleware component such as an application server, or a computing system that includes a front-end component such as a user computer with a graphical user interface or a web browser through which a user can interact with the systems and techniques described herein, or any combination of such back-end, middleware, or front-end components. The components of the system can be interconnected by digital data communications (e.g., a communications network) in any form or medium. Examples of communication networks include: local area networks (LANs), wide area networks (WANs), the Internet, and block-chain networks.

A computer system can include a client and a server. Clients and servers are generally located apart from each other and interact through communication networks. The client-server relationship is established by running computer programs on the respective computers that have the relationship. Servers can be servers for distributed systems or servers incorporating the block-chain technologies.

Artificial intelligence technologies enable computers to simulate certain human thought processes and intelligent behaviors such as learning, reasoning, thinking, planning, and the like. It encompasses both hardware and software technologies. Artificial intelligence hardware technologies generally include technologies such as sensors, specialized artificial intelligence chips, cloud computing, distributed storage, big data processing, and the like. Artificial intelligence software technologies primarily encompass several major areas, including computer vision, speech recognition, natural language processing, machine learning/deep learning, big data processing, knowledge mapping and the like.

It should be understood that various forms of the process as described above can be used, and operations may be reordered, added, or removed. For example, the operations described in the present disclosure can be executed in parallel, in sequence, or in a different order, as long as they achieve the desired results of the disclosed technologies, which is not limited by the present disclosure.

The above specific implementation does not constitute a limitation on the protection scope of the present disclosure. Those skilled in the art should understand that various modifications, combinations, sub-combinations and substitutions can be made according to design requirements and other factors. Any modification, equivalent replacement, improvement and the like made within the principle of implementations of the present disclosure shall be included in the present disclosure.

What is claimed is:

1. A method for sleep quality assessment using a wearable device, comprising:

obtaining, by a processor, physiological data of a subject comprising at least one of pulse rate, respiratory rate or heart rate acquired by a physiological sensor of the wearable device;

determining, by the processor, sleep data of the subject by performing sleep recognition on the physiological data of the subject;

extracting, by the processor, sleep feature data from the sleep data based on a reference core sleep period of the subject, wherein the reference core sleep period comprises an individual core sleep period of the subject reflecting a sleep habit or circadian rhythm of the subject and a collective core sleep period of a group in a designated geographic area to which the subject belongs, the collective core sleep period of the group reflecting a sleep habit or circadian rhythm of the group in the designated geographic area; and obtaining, by the processor, one or more parameters indicating a sleep quality of the subject based on the sleep feature data, wherein the method further comprises:

determining an in-bed state of the subject based on acceleration data acquired by the wearable device; and in response to the in-bed state indicating being in bed, causing the physiological sensor of the wearable device to acquire the physiological data of the subject for sleep quality analysis.

2. The method of claim 1, further comprising:

obtaining, by the processor, an acceleration signal during a predetermined time period acquired by an acceleration sensor of the wearable device;

extracting, by the processor, a motion feature and a posture feature from the acceleration signal; and determining, by the processor, the in-bed state of the subject during the predetermined time based on a first in-bed state monitoring result determined based on the motion feature and a second in-bed state monitoring result determined based on the posture feature, wherein the first in-bed state monitoring result is compared with the second in-bed state monitoring result to determine the in-bed state of the subject.

3. The method of claim 2, wherein determining, by the processor, the in-bed state of the subject during the predetermined time period based on the first in-bed state monitoring result determined based on the motion feature and the second in-bed state monitoring result determined based on the posture feature comprises:

in response to the first in-bed state monitoring result being different from the second in-bed state monitoring result and either of the first in-bed state monitoring result or the second in-bed state monitoring result indicating being not in bed, determining the in-bed state of the subject during the predetermined time period to be not in bed.

4. The method of claim 3, wherein the acceleration signal comprises a plurality of acceleration values at a plurality of moments, and wherein extracting the posture feature from the acceleration signal comprises:

determining a window acceleration corresponding to each of a plurality of time windows based on a plurality of acceleration values at the plurality of moments within the time window;

in a case where the window acceleration corresponding to a time window is within a specified range, determining an acceleration vector corresponding to the time window; and determining the posture feature of the subject during the predetermined time period based on the acceleration vector.

5. The method of claim 2, wherein the acceleration signal comprises acceleration values at a plurality of moments of the predetermined time period, and wherein extracting the motion feature of the subject from the acceleration signal comprises:

dividing the predetermined time period into a plurality of time windows based on a specified time length;

determining a parameter indicating an activity status of the subject corresponding to each time window based on a plurality of acceleration values at the plurality of moments within the time window; and obtaining the motion feature of the subject during the predetermined time period based on the parameter indicating an activity status of the subject corresponding to the plurality of time windows within the predetermined time period.

6. The method of claim 5, wherein the motion feature comprises at least one of:

a time interval between each time window and an adjacent previous activity change point, a sequence of parameters indicating the activity status of the subject corresponding to the plurality of time windows within the predetermined time period, or a number of windows corresponding to each activity status within the predetermined time period.

7. The method of claim 2, wherein the predetermined time period comprises a plurality of time segments, the motion feature of the subject during the predetermined time period comprises a motion feature corresponding to each of the plurality of time segments, and the posture feature of the subject during the predetermined time period comprises a motion feature corresponding to each of the plurality of time segments; and wherein determining the in-bed state of the subject during the predetermined time period comprises:

determining a third in-bed state monitoring result of the subject within each time segment based on a posture feature corresponding to the time segment;

determining a fourth in-bed state monitoring result of the subject within each time segment based on a motion feature corresponding to the time segment; and determining, based on the third in-bed state monitoring result and the fourth in-bed state monitoring result corresponding to each of the plurality of time segments within the predetermined time period, an in-bed state of the subject corresponding to each of the plurality of time segments within the predetermined time period.

8. The method of claim 7, wherein determining, based on the third in-bed state monitoring result and the fourth in-bed state monitoring result corresponding to each of the plurality of time segments within the predetermined time period, the in-bed state of the subject corresponding to each of the plurality of time segments within the predetermined time period comprises:

in response to at least one of the third or the fourth in-bed state monitoring results corresponding to an Ath time segment being out of bed, at least one of the third or the fourth in-bed state monitoring results corresponding to an $(i+m)^{th}$ time segment being out of bed, and m being less than a specified value, determining an in-bed state corresponding to each of the time segments between the $i^{th}$ time segment and the $(i+m)^{th}$ time segment to be out of bed, wherein both i and m are positive integers; or in response to at least one of the third or the fourth in-bed state monitoring results corresponding to a $j^{th}$ time segment being out of bed and at least one of the third or the fourth in-bed state monitoring results corresponding to one or more other time segments adjacent to the $j^{th}$ time segment being suspected to be out of bed, determining an in-bed state corresponding to one or more other time segments adjacent to the $j^{th}$ time segment being out of bed, wherein j is a positive integer.

9. The method of claim 1, wherein the in-bed state serves as a trigger condition for the physiological sensor to acquire the physiological data, such that the physiological sensor is configured to acquire the physiological data in response to the in-bed state indicating being in bed.

10. The method of claim 1, wherein extracting, by the processor, the sleep feature data based on the reference core sleep period of the subject and the sleep data comprises:

determining a first sleep feature of the subject based on the sleep data and the individual core sleep period;

determining a second sleep feature of the subject based on the sleep data and the collective core sleep period; and determining the sleep feature data based on the first sleep feature as well as the second sleep feature.

11. The method of claim 1, further comprising:

obtaining attribute information of the subject; and wherein obtaining, by the processor, the one or more parameters indicating the sleep quality of the subject based on the sleep feature data comprises:

obtaining the one or more parameters indicating the sleep quality of the subject based on the sleep feature data and the attribute information.

12. The method of claim 11, wherein obtaining the one or more parameters indicating the sleep quality of the subject based on the sleep feature data and the attribute information comprises:

inputting the sleep feature data and the attribute information into a sleep quality assessment model to obtain one or more parameters indicating a sleep discomfort symptom.

13. The method of claim 1, further comprising:

generating at least one sleep suggestion for the subject based on the one or more parameters indicating the sleep quality of the subject, wherein the at least one sleep suggestion comprises at least one of: suggested time to go to bed, suggested activities in bed, suggested activities before going to bed, suggested sleep duration, or suggested wakeup time.

14. An electronic device, comprising:

at least one processor; and a memory communicatively coupled to the at least one processor;

wherein the memory stores instructions executable by the at least one processor, and execution of the instructions by the at least one processor causes the at least one processor to perform the method of claim 1.

15. A wearable device, comprising:

at least one of an acceleration sensor and a physiological sensor;

one or more wearable accessories;

at least one processor; and a memory communicatively coupled to the at least one processor;

wherein the memory stores instructions executable by the at least one processor, and execution of the instructions by the at least one processor causes the at least one processor to perform the method of claim 1.

16. A non-transitory computer readable storage medium, having computer instructions stored thereon, wherein the computer instructions are configured to cause a computer to perform the method of claim 1.

17. A computer program product comprising a computer program, the computer program, when executed by a processor, implements the method of claim 1.

18. The method of claim 1, wherein one or more parameters indicating the sleep quality comprises a sleep quality score or sleep efficiency.

19. The method of claim 1, wherein obtaining, by the processor, the physiological data of the subject comprising at least one of pulse rate, respiratory rate or heart rate acquired by the physiological sensor of the wearable device further comprises:

obtaining, by the processor, an acceleration signal acquired by an acceleration sensor of the wearable device during a predetermined time period;

determining, by the processor, based on the acceleration signal, whether the subject is in a sleep quality assessment condition during the predetermined time period; and in a case where the subject is determined to be in the sleep quality assessment condition during the predetermined time period, obtaining, by the processor, the physiological data of the subject acquired by the physiological sensor of the wearable device, the physiological data comprising at least one of pulse rate, respiratory rate, or heart rate.

20. The method of claim 1, further comprising:

in response to determining that the subject is in a sleep state based on the physiological data, obtaining, by the processor, additional physiological data of the subject acquired by the physiological sensor of the wearable device.

* * * * *